United States Patent
Wallace et al.

(10) Patent No.: US 7,335,883 B2
(45) Date of Patent: Feb. 26, 2008

(54) IMAGING APPARATUS AND METHOD

(75) Inventors: Vincent Patrick Wallace, Cambridge (GB); Ruth Mary Woodward, Cambridge (GB); Donald Dominic Arnone, Cambridge (GB); Bryan Edward Cole, Cambridge (GB)

(73) Assignee: Teraview Limited (GB)

( * ) Notice: Subject to any disclaimer, the term of this patent is extended or adjusted under 35 U.S.C. 154(b) by 0 days.

(21) Appl. No.: 10/489,542

(22) PCT Filed: Jul. 29, 2002
(Under 37 CFR 1.47)

(86) PCT No.: PCT/GB02/03534

§ 371 (c)(1),
(2), (4) Date: Nov. 4, 2004

(87) PCT Pub. No.: WO03/023383

PCT Pub. Date: Mar. 20, 2003

(65) Prior Publication Data
US 2005/0082479 A1    Apr. 21, 2005

(30) Foreign Application Priority Data
Sep. 12, 2001  (GB) .................................. 0122052.4
Jan. 24, 2002  (GB) .................................. 0201614.5

(51) Int. Cl.
*G01N 21/17*  (2006.01)
(52) U.S. Cl. ...................................................... 250/330
(58) Field of Classification Search ................. 250/330
See application file for complete search history.

(56) References Cited

FOREIGN PATENT DOCUMENTS

| EP | 0 841 548  | 5/1998 |
|----|------------|--------|
| EP | 0 864 857  | 9/1998 |
| GB | 2 347 835  | 9/2000 |
| GB | 2 360 186  | 9/2001 |
| WO | WO 01/65240| 9/2001 |

OTHER PUBLICATIONS

Cole et al., Terahertz imaging and spectroscopy of human skin in vivo, Proceedings of the SPIE vol. 4276 (May 2001), pp. 1-10.*
International Search Report PCT/GB02/03534 Form PCT/ISA/210 dated May 13, 2003.

* cited by examiner

*Primary Examiner*—David Porta
*Assistant Examiner*—Shun Lee
(74) *Attorney, Agent, or Firm*—Ostrolenk, Faber, Gerb & Soffen, LLP

(57) ABSTRACT

A method of imaging a sample, the method comprising: (a) irradiating a sample with a pulse of electromagnetic radiation, said pulse having a plurality of frequencies in the range from 25 GHz to 100 THz; (b) determining a first parameter related to the amplitude of the radiation, which is either reflected from and/or transmitted by the sample, in the time domain; (c) calculating the value of the first parameter at a first time value relative to the value of the first parameter at a second time value which coincides with a physical feature of the dataset of the first parameter with respect to time; and (d) generating an image by plotting the value calculated in step (c) for different points of the sample.

48 Claims, 20 Drawing Sheets

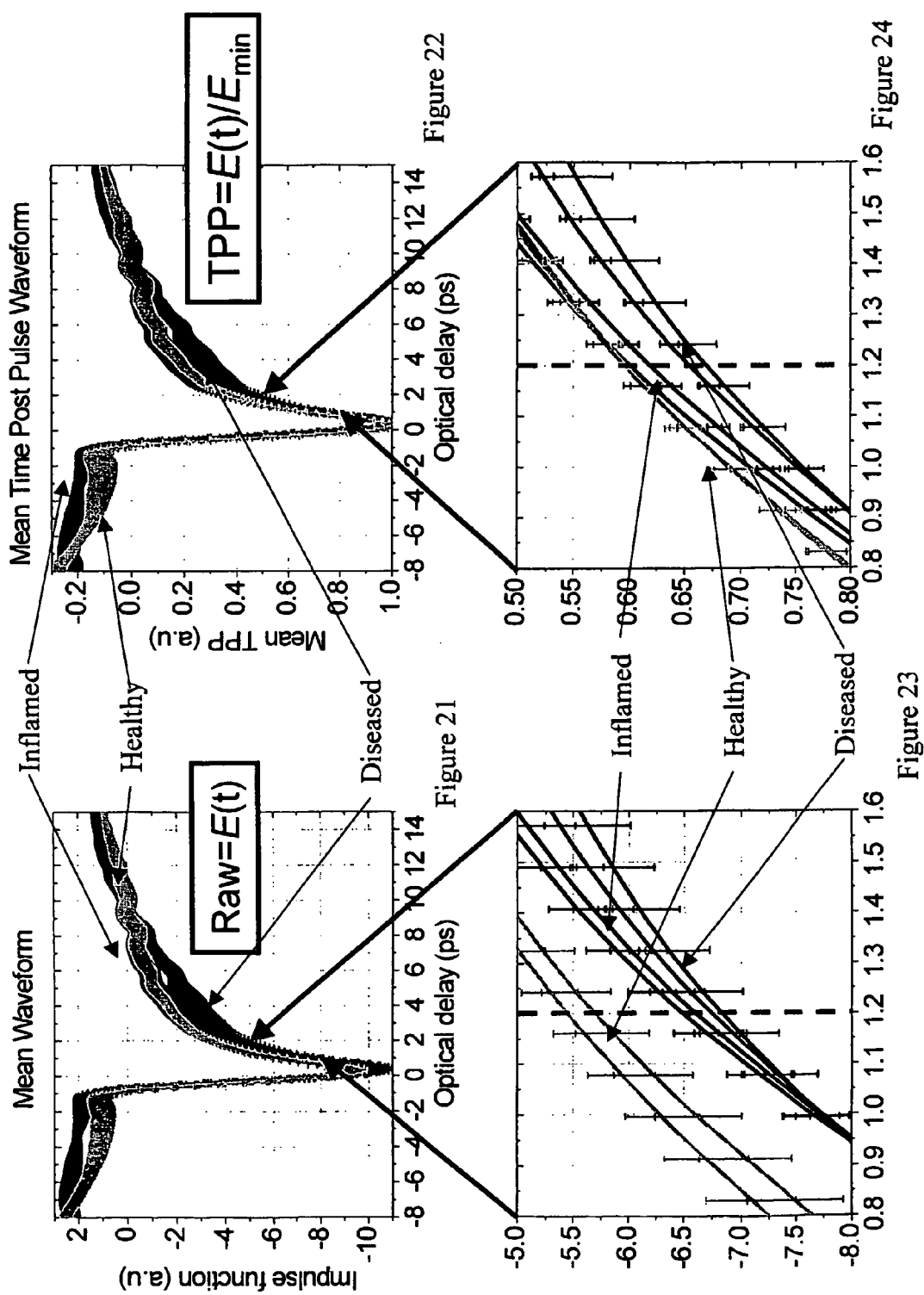

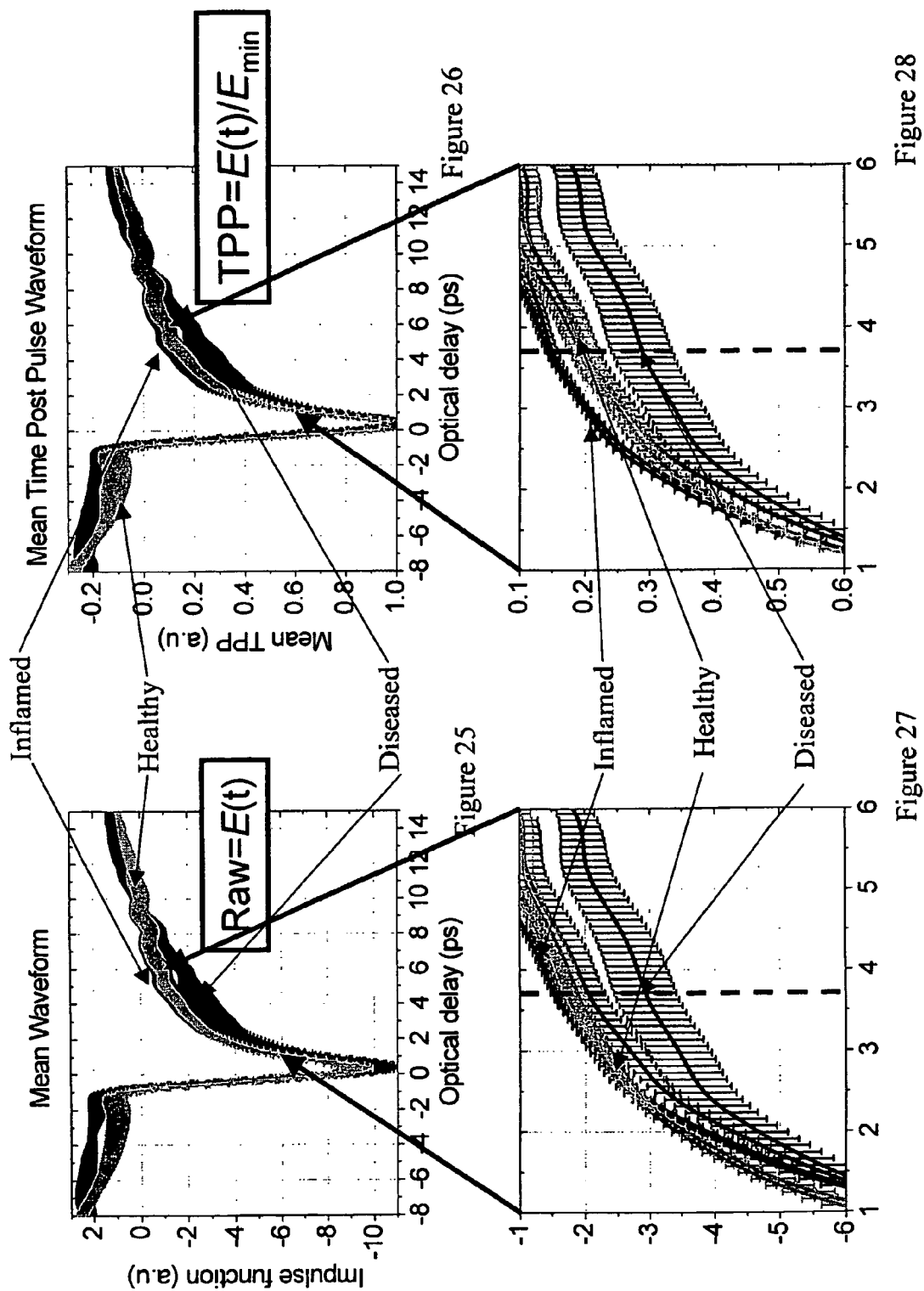

$t = 1.2$ ps $t = 3.7$ ps

IMAGING APPARATUS AND METHOD

BACKGROUND OF THE INVENTION

The present invention relates to the field of imaging samples with radiation in the infra-red (IR) and Terahertz frequency range and specifically using radiation in the higher Gigahertz (GHz) and the Terahertz (THz) frequency ranges. In this field, all such radiation is colloquially referred to as THz radiation, particularly that in the range from 25 GHz to 100 THz, more particularly that in the range of 50 GHz to 84 THz, especially that in the range from 100 GHz to 50 THz.

Such radiation is non-ionising and, as a result, it is particularly of use in medical applications. In medical imaging, the radiation is generally reflected from or transmitted through the patient.

Components of the sample being imaged will have a frequency dependent absorption coefficient and refractive index, thus each component of a sample subjected to radiation will leave its own characteristic fingerprint in the detected radiation. Thus, researchers have attempted to image samples using a plurality of frequencies to create an image from spectral information.

Measurements have been made using both frequency domain techniques, (where the amplitude of each frequency components is analysed), and time domain techniques, (where the radiation is analysed as a function of the delay time introduced by the sample into the path of the radiation). Time domain imaging is described in earlier patent GB 2 347 835.

For imaging, in the time domain, a time domain spectra is obtained for each pixel of the sample. It is then necessary to obtain a single parameter from each spectra to plot for each pixel. Previous attempts at producing images from such spectra have used the amplitude of the highest maximum or lowest minimum.

SUMMARY OF THE INVENTION

It is an object of the present invention to provide a method and apparatus which derives a parameter from time domain spectra to allow an image with enhanced contrast to be generated. The image can be a two dimensional image of an area of a sample, or it may be a profile of a line passing through the sample.

Thus, in a first aspect, the present invention provides a method of imaging a sample, the method comprising:

(a) irradiating a sample with a pulse of electromagnetic radiation, said pulse having a plurality of frequencies in the range from 25 GHz to 100 THz;

(b) determining a first parameter at least related to the amplitude of the radiation, which is either reflected from and/or transmitted by the sample, in the time domain;

(c) calculating the value of the first parameter at a first time value relative to the value of the first parameter at a second time value, wherein the second time value coincides with a physical feature of the first parameter with respect to time; and (d) generating an image by plotting the value calculated in step (c) for different points of the sample.

As previously described, the image may be just a profile through the sample or a full 2D image of an area of the sample or even a 3D image of a volume of the sample.

The inventors have found that the method of the present invention has produced surprisingly good results for identifying the extent of tumours and particularly Basal Cell Carcinoma (BCC) which is the most common form of skin cancer in caucasians. BCCs seldom metatise, but they can be locally invasive and with 80% occurring on the head and neck, their effects on the patient can be cosmetically traumatic.

The value of the first parameter at a first time value is calculated relative to the value of the first parameter of the second time value. The second time value is chosen to coincide with a physical feature of the dataset with respect to time such as a minima, maxima, zero-crossing point, point of inversion, discontinuity etc.

The second time value preferably corresponds to a predetermined maxima or minima of the first parameter with respect to time.

For example, the value of the first parameter at the first time value, i.e. $E(t_1)$ may be divided or multiplied by the value of the first parameter at the second time value i.e. $E(t_2)$. Alternatively, these two values may be added or subtracted from one another. Some further numerical relationship may also be implemented.

It has been found for imaging tumours and especially BCCs that good contrast can be obtained if Z is plotted where Z:

$$Z = \frac{E(t_1)}{E(t_2)}$$

Preferably, $t_1$ is chosen as one of the time values ascending or descending to or from a local maxima or minima where $t_2$ is chosen to coincide with this local maxima or minima.

In a particularly preferred configuration, the first time value is chosen from the subsequent time values ascending from a local minima, where $t_2$ is chosen to coincide with that minima.

When constructing the image, it is necessary to derive Z for each pixel of the sample of interest. $t_2$ is tied to a physical feature of the time domain plot of the first parameter which may move in time from point to point. For example, $t_2$ may coincide with a minima which shifts slightly from point to point. The first time value $t_1$ may be fixed in time or may be located at a fixed time interval $\delta t$ from $t_2$ such that $t_1$ moves with $t_2$ from point to point of the sample.

The first time value may be chosen to coincide with the signal received from a point of interest within the sample. For example, if the sample is measured using reflection geometry, the first value may coincide with the time in which the reflected pulse takes the reach the part of interest in the sample, e.g. if the sample is a BCC sample, the time which it takes to be reflected from the tumour. If $t_2$ is chosen to coincide with a main minima obtained using reflection geometry, $\delta t$ may be chosen as approximately the time which the radiation takes to travel from the sample surface to the tumour and back to the surface. In practice, due to variations in the composition of the sample, $t_1$ will be determined experimentally.

As the contrast can be optimised by careful selection of the first time value, preferably, the method further comprises the step of determining the first parameter for a plurality of first time values and calculating these values of the first parameter relative to the value of the first parameter at the second time value. The method then further comprising the step of generating an image of the sample for each of the said first time values.

Thus, by viewing each of the images, an optimum first time value can be determined. Alternatively, each image may be analysed by means of a computer in order to derive the best value of $t_1$ using computer means.

If $t_1$ is fixed for each point in a single image, then the image may be optimised by finding the optimum value of the fixed $t_1$. If $t_1$ is a located fixed time interval $\delta t$ from $t_2$ for each point in the image, then the image may optimised by finding the optimum value of the time interval, $\delta t$.

Good contrast may also be obtained by careful choice of the fixed time interval between the first and second time values regardless of whether or not the second time value corresponds to a physical feature of the time domain data set. Thus, in a second aspect, the present invention provides a method of imaging a sample, the method comprising:

(a) irradiating a sample with a pulse of electromagnetic radiation, said pulse having a plurality of frequencies in the range from 25 GHz to 100 THz;

(b) determining a first parameter related to the amplitude of the radiation, which is either reflected from and/or transmitted by the sample, in the time domain;

(c) calculating the value of the first parameter at a first time value relative to the value of the first parameter at a second time value; and (d) generating an image by plotting the value calculated in step (c) for different points of the sample, wherein the time interval between the first and second time values is constant for all points used to generate the image.

The value of the first parameter for the first time value with respect to the second time value may be calculated using any of the methods suggested in relation to the first aspect.

As enhanced contrast may be obtained by measuring the time domain signal at just two points, the image acquisition time may be substantially reduced. However, in some cases, it may be necessary to still acquire the data for more than two time values in order to derive the first parameter.

The first parameter may be the amplitude of the radiation itself. However, preferably, the detected amplitude is processed in order to obtain a first parameter.

When imaging non-rigid samples, it is preferable if a flat surface is provided for receiving the radiation. This is typically provided by a member such as a window which is transparent to the irradiating radiation. The sample is then pressed against this window to provide a flat analysis surface. However, the window itself can cause its own problems. This is because the window, has two interfaces, a front interface upon which the irradiating radiation is directly incident and a back surface which abuts the sample. Both of these surfaces will reflect radiation given rise to at least two unwanted signals in the detected reflected radiation. We refer to at least two reflections because multiple internal reflections may occur within the window giving even further unwanted effects.

Preferably, if the sample is irradiated through such a member, steps are taken in order to remove this so-called "baseline" signal. Thus, if step (a) comprises a step of irradiating the sample through a member which is transparent to the irradiating radiation and which abuts the sample, the method preferably further comprises the step of obtaining a baseline signal by irradiating a member in the absence of the sample and detecting the amplitude of the reflected radiation. The first parameter is then determined by subtracting the baseline signal from the detected amplitude of the reflected radiation from both the member and the sample.

The baseline signal can be subtracted from the amplitude of the detected reflected radiation in the time domain or the frequency domain. The frequency domain signal is created by Fourier transforming the time domain signal.

In addition to or as an alternative, it may also be desirable to obtain a reference signal which is obtained by replacing the sample with the reference object of known reflectance or transmittance and measuring the amplitude of radiation reflected from the reference object (if the sample is to be measured in reflectance mode) or the transmittance of the object (if the sample is to be measured in transmission mode). The first parameter is then derived by dividing the detected amplitude of the radiation from the sample with the reference signal in the frequency domain.

Where both a reference signal and a baseline signal are obtained, the baseline signal is subtracted from both the sample signal and the reference signal and the baseline subtracted sample signal is then divided by the baseline subtracted reference signal. This division is performed in the frequency domain.

It is possible to interchange the reference and baseline signals. For example, the baseline signal may be obtained by replacing the sample with an object of known reflectance or transmittance, for example, a Quartz window and the reference signal may be obtained in the absence of a sample or a reference object.

Preferably, the amplitude of the detected radiation or the amplitude of the detected radiation which has been baseline subtracted and/or divided by a reference signal is then filtered. More preferably, this is achieved by multiplying the amplitude which may have been baseline subtracted and/or divided by a reference signal in the by the complex Fourier transform of a filter function $F(t)$, where $F(t)$ is a non-zero function whose integral between time limits $t_a$ and $t_b$ is zero, and where $t_a$ and $t_b$ are chosen to encompass the part of interest of the reflected or transmitted pulse of radiation.

To clarify, radiation is supplied to the sample in the form of a pulse. The pulse will have a finite length. As the pulse passes through free space and through the sample, the length of the pulse may change. It is important to set $t_a$ and $t_b$ so that integration is performed over the part of the pulse of interest.

Considering the case of transmission, if the sample has the same properties as free space, then the radiation will pass through the sample without any delay. However, if the sample introduces a time delay into the beam, then $t_a$ will be set to a negative value which has a magnitude is equal to or larger than the expected value of this time delay. $T_b$ will generally, be set to the positive value of $t_a$.

Similarly, during reflection, $t_a$ will be set to a negative value which has a magnitude is equal to or larger than the expected value of this time delay introduced by the pulse being reflected from the deepest point of interest in the sample. $t_b$ will generally, be set to the positive value of $t_a$.

Generally, the method of the above aspect of the present invention will be performed using the above described apparatus where the radiation is measured using a reference beam and wherein a scanning delay line is introduced into the path of the reference beam or irradiating beam in order to measure the phase change introduced by the sample. In this situation, $t_a$ and $t_b$ will be the negative and positive limits of the scanning delay line. These may be set to the duration of the pulse or possibly a shorter time range.

Preferably function $F(t)$ comprises a Gaussian component. Generally, $t_a$ and $t_b$ are symmetric about 0, preferably $F(t)$ is also symmetric about zero.

As the signal is usually digitally sampled, strictly a summation is performed as opposed to an integral.

A particularly preferable form of F(t) is provided by:

$$F(t) = \frac{2}{\pi}\left\{\frac{e^{-2\left(\frac{t}{\alpha}\right)^2}}{\alpha} - \frac{e^{-2\left(\frac{t}{\beta}\right)^2}}{\beta}\right\}$$

where α and β are constants.

Preferable α is substantially equal to the shortest pulse length of the beam of pulsed radiation and β is set to be much longer than the pulse length, typically 5 to 100 times the pulse length. However, both of these values will generally be optimised by the operator.

If β is greater than or comparable to the time which it takes the radiation to penetrate the sample to the point of interest then, F(t) can take the simplified form:

$$F(t) = \frac{2}{\pi}\left\{\frac{e^{-2\left(\frac{t}{\alpha}\right)^2}}{\alpha} - \frac{1}{T}\right\}$$

where α is a constant which is substantially equal to the shortest pulse length of the beam and T is substantially equal to the time which it takes the beam of radiation to penetrate to the deepest point of interest in the sample.

A sample signal which has been baseline subtracted, divided by a reference signal and filtered is referred to as the impulse function. Preferably, the first parameter is the impulse function.

As the present invention is concerned with producing an image, the actual value of the impulse function at a pixel does not have to have a strong numerical correlation with a physical parameter of the sample. However, it is important that the impulse function is capable of showing variations in the composition of the sample.

The first time value may be determined by:
  (i) selecting n regions of said sample, where n is an integer of at least 2;
  (ii) producing n time domain spectra of a second parameter which is at least related to the amplitude of the radiation reflected from and/or transmitted by the sample, where the nth spectra is obtained by averaging the second parameter across the nth area and plotting this averaged value, as it varies with delay time;
  (iii) determining the first time value by comparing at least two of the n spectra derived in step (ii).

Preferably, each spectra is normalised to the value of the second parameter at a time value which coincides with a physical feature of the second parameter with respect to time, prior to comparing the spectra. A physical feature of the spectra of the second parameter may be a minimum, maximum, point of inflection etc. Preferably, the same physical feature is chosen which identifies the second time value.

The spectra may be compared by performing a mathematical operation on at least two of the spectra. For example, the spectra may be divided by or subtracted from one another.

The selected regions may be lines or areas of the sample. They may be continuous lines or areas or discontinuous lines or areas. The regions may be of the same size of different sizes and may comprise any number of pixels.

Preferably, the regions selected by first generating a preliminary image of an area of the sample by plotting a preliminary imaging parameter which is at least related to the amplitude of the reflection reflected from and/or transmitted by the sample.

The preliminary imaging parameter may be any parameter which can be used to generate an image of the sample, for example, it may be the value of the first parameter and/or a second parameter, at a minima, maxima or point of inflection, etc. Alternatively, it may be the value of the first parameter or second parameter at an arbitrary time value or a time value which has previously been used to show contrast in the sample or similar samples.

In the simplest case, just two areas are selected. However, the method may also be used to optimise contrast between 3 or more different regions. To achieve this, three regions are chosen, the value of the preliminary imaging parameter differing between said three selected regions, the first time value being chosen to coincide with a region where there is a difference between the three spectra.

The first parameter and second parameter may be the same or different. The second parameter may be preferably chosen from any of the parameters previously described in relation to the first parameter.

Regions of the sample may be chosen at random or, alternatively, regions of the sample may be chosen where some contrast has already been observed. In this example, the n areas are chosen such that the level of the preliminary imaging parameter within each region is substantially constant and the level of the preliminary imaging parameter is different between at least two of the regions.

Preferably, a standard deviation of about 30% in the primary imaging parameter is allowed within a selected region, more preferably 20%, even more preferably 10%.

The areas may be selected randomly by a person. Alternatively, the area selection may be automated. For example, a processor may be used to select n regions at random or sequentially and then compare the spectra from these regions in order to optimise the time value. The processor is preferably configured to select each area such that the preliminary imaging parameter is substantially constant within each area as previously described. The processor may further be configured to vary the size of the selected region in order to select regions which fall within the above criteria.

The above method of deriving a first time value may also be advantageously used with the method described in GB 2 360 186. Thus, in a third aspect, the present invention provides a method of imaging a sample, the method comprising:
  (a) irradiating a sample with a pulse of electromagnetic radiation, said pulse having a plurality of frequencies in the range from 25 GHz to 100 THz;
  (b) determining a first parameter at least related to the amplitude of the radiation, which is either reflected from and/or transmitted by the sample, in the time domain; and
  (c) generating an image of the sample by plotting the value of the first parameter at a first time value, said first time value being determined by:
    (i) selecting n regions of said sample, where n is an integer of at least 2,
    (ii) producing n time domain spectra of a second parameter which is at least related to the amplitude of the radiation reflected from and/or transmitted by the sample, where the nth spectra is obtained by averaging the second parameter across the nth area and plotting this averaged value, as it varies with delay time;

(iii) determining the first time value by comparing at least two of the n spectra derived in step (ii).

In a fourth aspect, the present invention provides imaging apparatus comprising:

a source for irradiating a sample with a pulse of electromagnetic radiation, said pulse having a plurality of frequencies in the range from 25 GHz to 100 THz;

a detector for detecting the amplitude of radiation which is either reflected from or transmitted by the sample;

means for determining a first parameter which is related to the amplitude of the reflected and/or transmitted radiation in the time domain;

calculating means for calculating the value of the first parameter at a first time value relative to the value of the first parameter at a second time value, wherein the second time value coincides with a physical feature of the dataset of the first parameter with respect to time; and means for generating an image by plotting the value calculated by the calculating means for different points of the sample.

In a fifth aspect, the present invention provides an apparatus for imaging a sample, the apparatus comprising:

a source for irradiating a sample with a pulse of electromagnetic radiation, said pulse having a plurality of frequencies in the range from 25 GHz to 100 THz;

detector means for detecting the amplitude of radiation reflected from and/or transmitted by the sample;

means for determining a first parameter related to the amplitude of the radiation in the time domain;

calculating means for calculating the value of the first parameter at a first time value with respect to the value of the first parameter at a second time value, and imaging means for generating an image by plotting the value calculated by the calculating means for different parts of the sample, wherein the time interval between the first and second time intervals is constant for all points used to generate the image.

The detector may be a direct detector of THz radiation or an apparatus according to any of the above three aspects of the invention, the detector may be a direct detector of THz radiation or it may be of the type which converts THz radiation into an easily readable signal.

For example, the detector may comprise a non-linear crystal which is configured such that upon irradiation of a probe beam and a THz beam, the polarisation of the probe beam is rotated. The probe beam can be of a frequency which can be easily measured (for example near infra-red). Typical crystals which exhibit this effect, the so-called "AC Pockels" effect are GaAs, GaSe, $NH_4H_2PO_4$, ADP, $KH_2PO_4$, $KH_2ASO_4$, Quartz, $AlPO_4$, ZnO, CdS, GaP, $BaTiO_3$, $LiTaO_3$, $LiNbO_3$, Te, Se, ZnTe, ZnSe, $Ba_2NaNb_5O_{15}$, $AgAsS_3$, proustite, CdSe, $CdGeAs_2$, $AgGaSe_2$, $AgSbS_3$, ZnS, organic crystals such as DAST (4-N-methylstilbazolium. This type of detection mechanism is generally referred to as 'Electro-optic sampling' or EOS.

Alternatively, the detector could be a so-called photoconducting detector. Here, the detector comprises a photoconductive material such as low temperature grown GaAs, Arsenic implanted GaAs or radiation damaged Si on Sapphire. A pair of electrodes, for example in a bow-tie configuration or in a transmission line configuration are provided on a surface of the photoconductive material. When the photoconductive material is irradiated by the reflected radiation and also, the probe beam, a current is generated between the two electrodes. The magnitude of this photovoltage current is an indication of the magnitude of the THz signal.

Although it is possible to generate THz radiation directly, the most effective THz generation can be achieved by converting a pump beam into a THz beam. To do this, the source comprises a frequency conversion member and a source of a pump beam.

There are many possible options for the frequency conversion member. For example, the frequency conversion member may comprise a non-linear member, which is configured to emit a beam of emitted radiation in response to irradiation by a pump beam. Preferably, the pump beam comprises at least two frequency components, (or two pump beams having different frequencies are used), the non-linear member can be configured to emit an emitted beam having a frequency which is the difference of the at least two frequencies of the pump beam or beams. Typical non-linear members are: GaAs or Si based semiconductors. More preferably, a crystalline structure is used. The following are further examples of possible materials:

$NH_4H_2PO_4$, ADP, $KH_2PO_4$, $KH_2ASO_4$, Quartz, $AlPO_4$, ZnO, CdS, GaP, $BaTiO_3$, $LiTaO_3$, $LiNbO_3$, Te, Se, ZnTe, ZnSe, $Ba_2NaNb_5O_{15}$, $AgAsS_3$, proustite, CdSe, $CdGeAs_2$, $AgGaSe_2$, $AgSbS_3$, ZnS, GaSe or organic crystals such as DAST (4-N-methylstilbazolium).

In order to produce an emitted beam having a frequency in the THz regime, preferably the at least two frequencies of the pump beam or beams are in the near infra-red regime. Typically, frequencies between $0.1 \times 10^{12}$ Hz and $5 \times 10^{14}$ Hz are used.

Alternatively the frequency conversion member is a photoconducting emitter, such an emitter comprises a photoconductive material such as low temperature grown or arsenic implanted GaAs or radiation damaged Si or Sapphire.

Electrodes which may be of any shape such as a dipole arrangement, a double dipole arrangement, a bow-tie arrangement or transmission line arrangement are provided on the surface of the photoconductive material. At least two electrodes are provided. Upon application of a bias between the electrodes and irradiation of a pump beam(s) having at least two different frequency components, a beam of radiation is emitted having a frequency different to that of the at least two frequency components of the pump beam or beams.

When a pulse having a plurality of frequencies passes via a sample to a detector, the various frequencies will not arrive at the detector at the same time due to the frequency dependent response of the sample. A time domain signal can be established by measuring the amplitude of the detected radiation with respect to time. In order to achieve this, it is preferable if a scanning delay line is inserted into either the path of the probe or pump beam. The delay line can be configured to scan over the whole length of the pulse.

As mentioned with respect to the method of the present invention, the first time value can be selected in order to optimise contrast in the image. The first time value may be fixed with respect to zero across an image, or it may be fixed with respect to the second time value.

Therefore, preferably, the apparatus further comprises means for generating a plurality of images corresponding to different first time values, the apparatus also comprising means for scanning through said images by varying said first time value in order to determine a first time value which allows the best contrast.

The apparatus preferably further comprises:

(i) means for selecting n regions of said sample, where n is an integer of at least 2;

(ii) means for producing n time domain spectra of a second parameter which is at least related to the amplitude of the radiation reflected from and/or transmitted by the sample, where the nth spectra is obtained by averaging the second parameter across the nth area and plotting this averaged value as it varies with delay time; and (iii) means determining the first time value by comparing at least two of the n spectra.

In a sixth aspect, the present invention provides:

(a) means for irradiating a sample with a pulse of electromagnetic radiation, said pulse having a plurality of frequencies in the range from 25 GHz to 100 THz;

(b) means for determining a first parameter, at least related to the amplitude of the radiation, which is either reflected from and/or transmitted by the sample, in the time domain; and (c) means for generating an image of the sample by using the value of the first parameter at a first time value, said apparatus being configured to determine said first time value by:

(i) selecting n regions of said sample, where n is an integer of at least 2;

(ii) producing n spectra in the time domain, where the nth spectra is obtained by plotting the second parameter, averaged across the nth area, against delay time;

(iii) determining the first time value by comparing at least two of the n spectra.

The means for selecting regions may be automatic means. For example, a program may be executed to select two or more regions of the sample at random or two or more regions of the sample which have the largest difference between their mean colour levels, the standard deviation of these areas may be calculated to ensure that the selected area does not cover an area of high contrast.

Alternatively, the apparatus may be provided with means which allow an operator to select two or more areas. For example, the apparatus may be configured to support a cursor which the operator may use to select particular areas of the image.

BRIEF DESCRIPTION OF THE DRAWINGS

The present invention will now be described with reference to the preferred non-limiting embodiments in which:

FIG. 21 illustrates a plot of the mean impulse function in the time domain for areas s1, s2, d1, d2, h1 and h2 of FIG. 19;

FIG. 22 illustrates a plot similar to that of FIG. 21 where the spectra have been normalised to the value E(min);

FIG. 23 illustrates a detail of the plot of FIG. 21;

FIG. 24 illustrates a detail of the plot of FIG. 22;

FIG. 25 is a plot identical to that of FIG. 21 but repeated to allow easy comparison;

FIG. 26 is a plot identical to that of FIG. 22 but repeated to allow easy comparison;

FIG. 27 illustrates a detail of the plot of FIG. 25;

FIG. 28 illustrates a detail of the plot of FIG. 26;

FIG. 1 shows a basic THz reflection imaging system. The system can be split into three main sections: a generation section 1, an imaging section 3 and a detection section 5.

Figure 1:
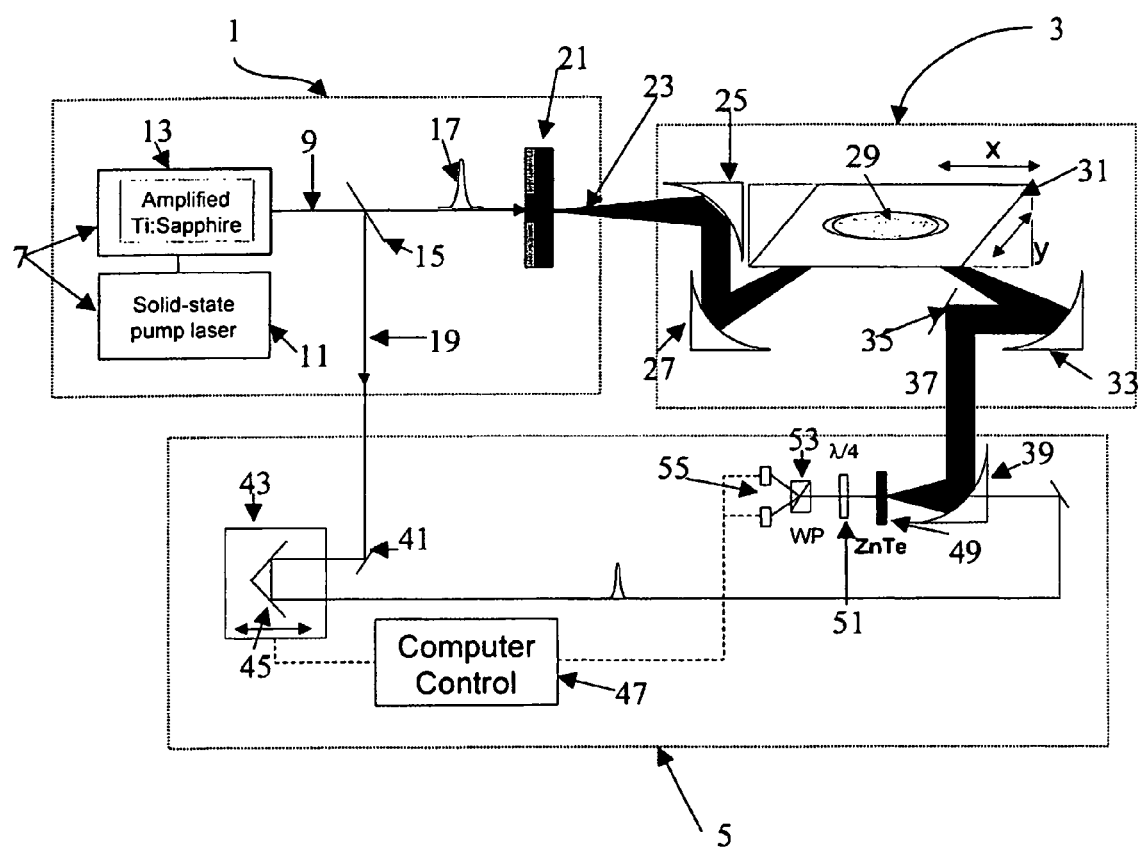
FIG. 1 is a schematic of a reflection imaging system which may be used in accordance with an embodiment of the present invention.

A THz beam of radiation is produced in generating section 1. Generation section 1 comprises an optically amplified Ti:Sapphire laser 7 to produce a beam 9 of 250 fs pulses at 800 nm.

The optically amplified laser 7 comprises a solid state pump laser 11 and an amplified Ti:Sapphire section 13. Beam 9 is divided by 50:50 beam splitter 15. Beam splitter 15 divides the beam into a pump pulse 17 which is used to generate THz radiation and a probe pulse 19 which is used in the detection of the radiation reflected from the sample.

THz pulses are generated by optical excitation and charge acceleration of biased GaAs stripline antenna 21 which outputs THz pulses 23 which have a bandwidth of 0.1 THz to 3 THz. The emitted beam 23 is then passed into imaging section 3.

The irradiating THz beam 23 is then directed via first off-axis parabolic mirror 25 onto second off-axis parabolic mirror 27 and then focussed to a 400 µm spot on sample 29. Sample 29 is mounted on motorised stage 31. The sample mount 31 is computer controlled and can be configured to move the sample such that each section (pixel) of the sample in question can be imaged.

The reflected radiation is then collected via third off-axis parabolic mirror 33 and reflected via planar mirror 35 into the detection system 5. In the detection system, the reflected radiation 37 is reflected off-axis parabolic mirror 39. Off-axis parabolic mirror 39 has a hole through it which allows the reflected beam 37 to be combined with the probe beam 19 obtained by beam splitter 15.

Prior to combining the probe beam 19 with the reflected radiation 37 at off-axis parabolic mirror 39, the probe beam 19 is reflected off planar mirror 41 into scanning delay line 43. Scanning delay line comprises cuboid mirror 45 which moves back and forth under computer control 47 in order to vary the pulse length of the probe beam 19 with respect to the pump beam 17 and hence the irradiating and reflected radiation. Thus, the relative phase of the probe beam 19 can be varied with respect to the pump pulse 19.

The combined probe beam and reflected radiation 37 is then collimated and focused onto ZnTe detection crystal 49. The THz radiation is detected using the linear electro-optic Pockel's effect.

The linearly polarised probe beam 19 has its polarisation oriented such that it has components along both the ordinary and extra-ordinary axis of detection crystal 49. Each of the axis has distinct refractive indices $n_0$ and $n_r$ along the ordinary and extra-ordinary axis of the crystal 49 respectively. In the absence of reflected radiation 37, the linearly polarised probe beam 19 passes through the detection crystal with a negligible change in its polarisation.

The applicant wishes to clarify that the angle through which the polarisation is rotated is negligible. However, the linearly polarised beam can become slightly elliptical. This effect is compensated for by a variable retardation waveplate, for example, quarter waveplate 51.

The beam emitted by detection crystal 49 is converted into circularly polarised beam by quarter waveplate 51. The beam is then split into two linearly polarised beams by Wollaston prism 53 (or an equivalent device for separating orthogonal polarisation components) which directs the two orthogonal components of the polarised beam onto a balance photo diode assembly 55. The balance photo diode signal is adjusted using waveplate 51 so that the difference in outputs between the two diodes is zero when only the probe beam 19 is incident on the detection crystal 49.

However, if the detector also detects reflected radiation 37, the angle through which the polarisation is rotated by is not negligible. This is because the THz electric field modifies the refractive index of the probe beam 19 along one of the axis $n_e$, $n_o$. This results in the physical field emitted by detection crystal 49 being elliptical. Therefore, the polarisation components separated by prism 53 are not equal and the difference in voltage between the output diodes of balance photo-diode assembly 55 gives a detection voltage.

The rotation in the polarisation is obscured if the phase of the reflected radiation 37 reaching the detection crystal 49 is different to the phase of the probe beam 19. As the sample 29 will introduce a different phase change for different frequency components of the irradiating radiation 23, the delay line 43 is swept under control of computer 47 in order to sweep the phase of the probe beam 19 with respect to the reflected radiation 37 and hence detect the delay time of each of the frequency components of reflected radiation 37. This produces a so-called time-domain signal.

Computer control 47 also is used to control the movement of stage 31 in order to ensure that a full data set is collected for each pixel of interest of sample 29.

Figure 2:
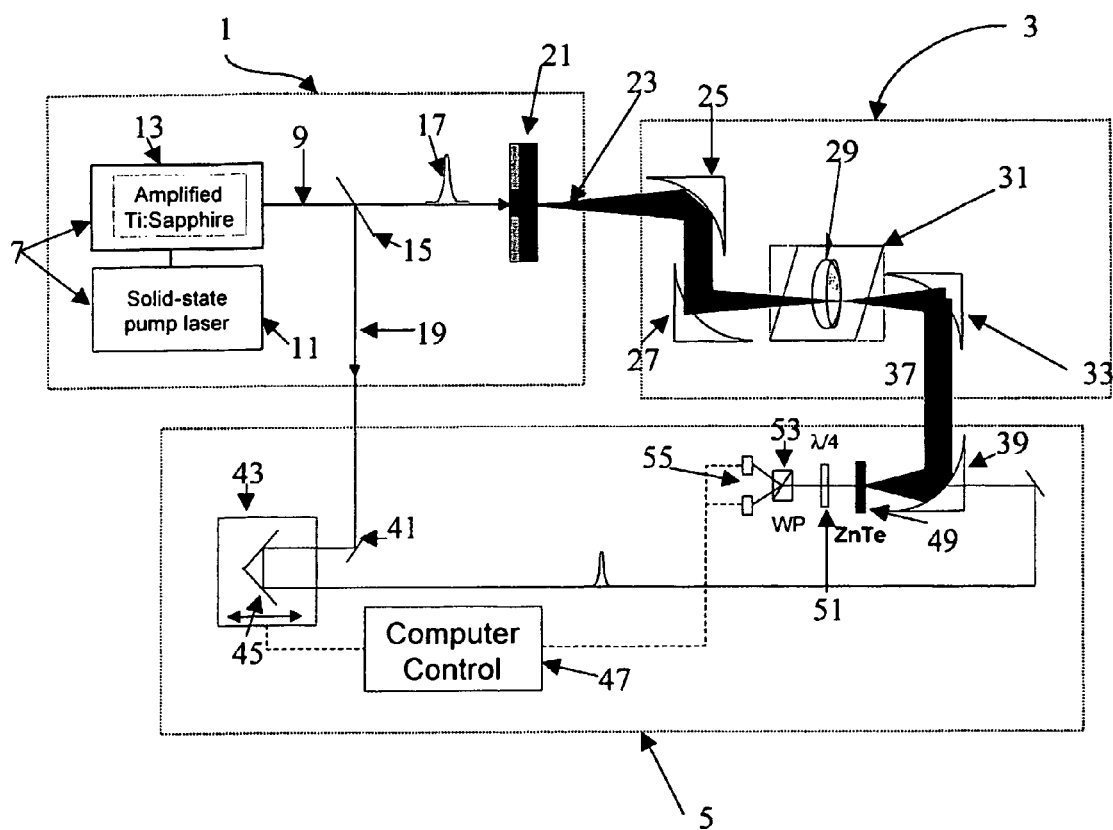
FIG. 2 is a is a schematic of a transmission imaging system which may be used in accordance with an embodiment of the present invention.

The above system illustrates is configured for reflection measurements. However, it will be appreciated that those skilled in the art that the system could also be adapted for a transmission method. Such an apparatus is shown in FIG. 2. To avoid unnecessary repetition, like reference numerals will be used to denote like features. In imaging section 3, first 25 and second 27 parabolic mirrors are configured to focus radiation onto sample 29. The third parabolic mirror 23 then collects the transmitted radiation and directs it into detection section 5. The generation 1 and detection 5 sections are the same as those for the reflection apparatus of FIG. 1.

Figure 3:
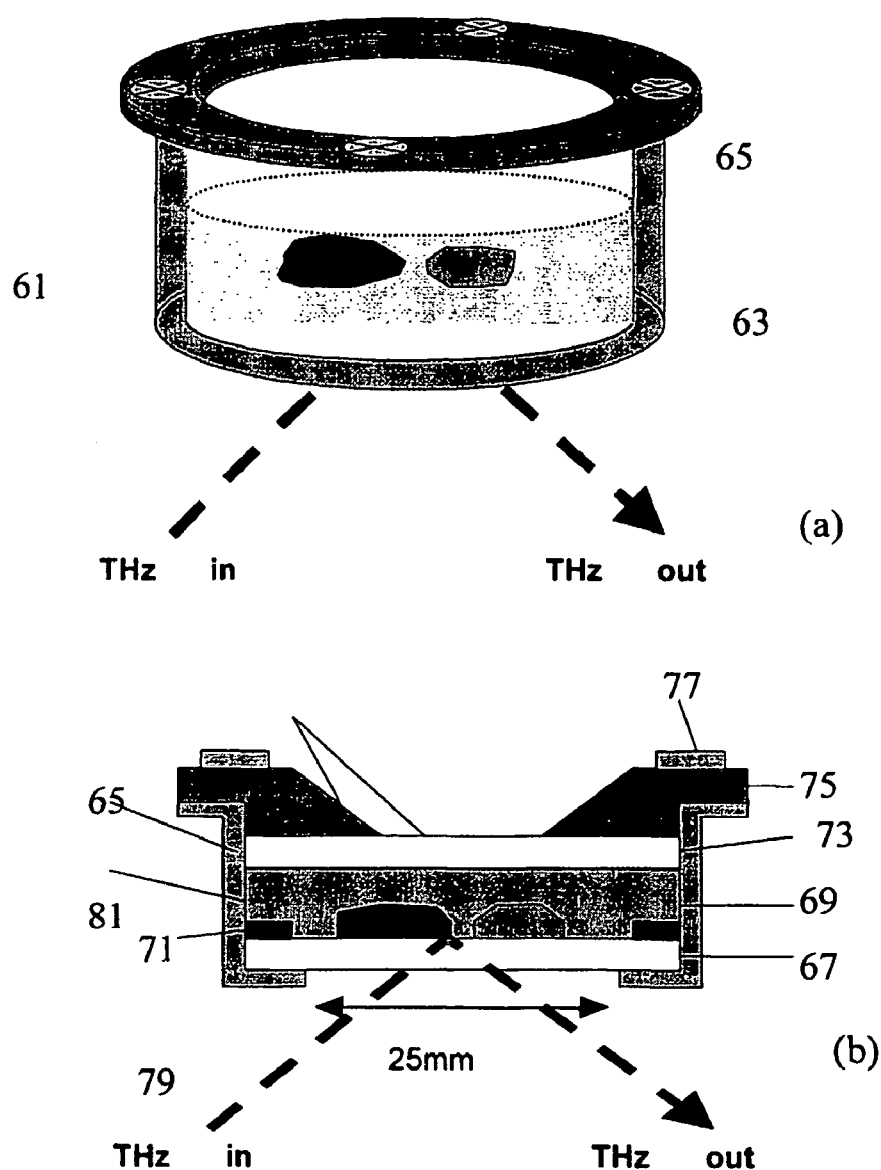
FIG. 3a is a perspective view of a sample holder and FIG. 3b is a plan view of a sample holder which may be used in accordance with an embodiment of the present invention.

The method of the present invention has been found to be of particular use in imaging Basal Cell Carcinoma. FIG. 3 illustrates a preferred mounting method for a sample of this type. FIG. 3a shows a perspective view of the sample holder whereas FIG. 3b shows a cross section of the sample holder.

FIGS. 3a and 3b show two samples 61 and 63 located in a hollow, cylindrical sample holder 65. The sample holder 65 is based on a modified liquid cell of the type used for Fourier transform infra-red spectrometry. The liquid cell is cylindrical in shape and comprises the hollow cylindrical container 65, a 2 mm thick Quartz plate 67 with a diameter of 25 mm, is placed at the base of container 65. The THz radiation irradiates the sample through Quartz window 67.

As water is a strong absorber of radiation in the THz regime, excess fluid is removed from the sample using lint free paper. The samples were mounted on the Quartz window 67 using tweezers and the top surface of the skin was placed on Quartz window 67. Sponge 69 is then placed on top of the sample so that the samples are sandwiched between the sponge 69 and Quartz window 67. The retaining ring 71 is placed on top of Quartz window 67 in order to keep the window level and also to maintain the position of the samples 61 and 63.

A polythene window 73 is provided on the opposing side of the sponge to the Quartz window and in contact with the sponge. The polythene window is held in place by retainer plate 75 which is screwed into the sample holder 65 by screw 77. This construction provides an airtight holder for the sample which prevents the sample from drying out during imaging.

Figure 4:
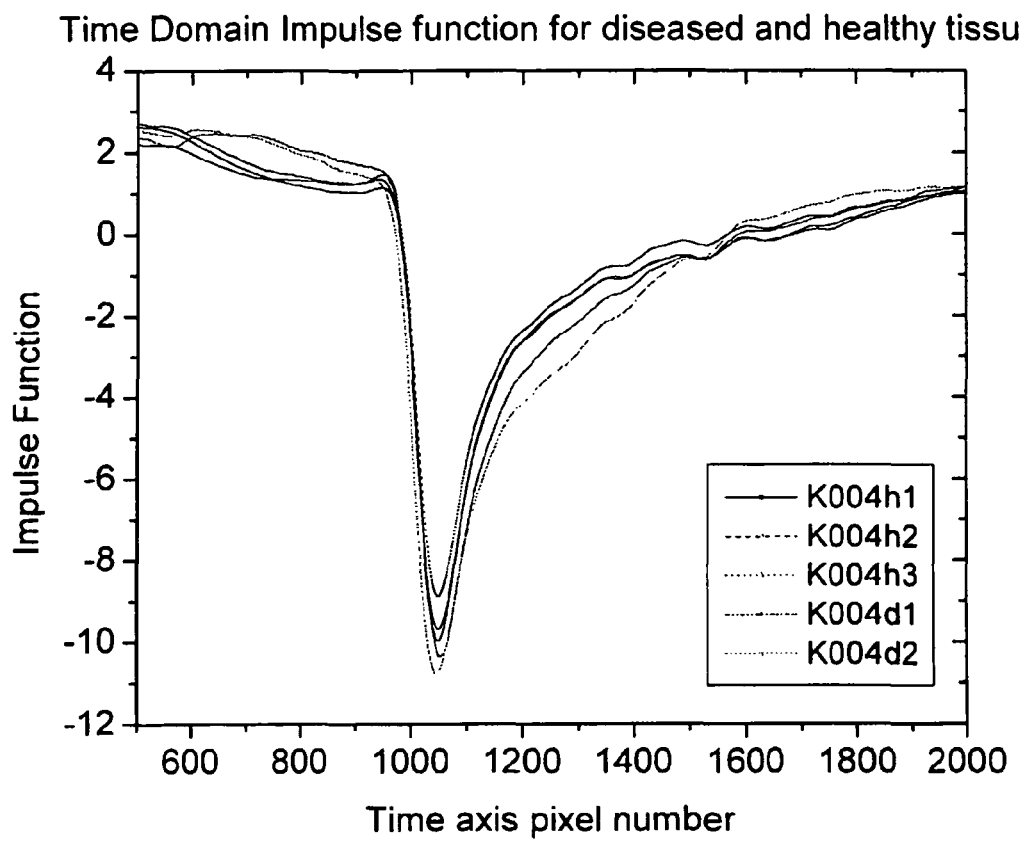
FIG. 4 illustrates a plurality of deconvoled impulse functions for a sample of a skin tumour.

FIG. 4 illustrates a time domain impulse function for diseased and healthy tissue. FIG. 4 shows the impulsed function along the y axis plotted against time delay (arbitrary units) along the x axis. Five traces are shown in FIG. 4 for five different pixels.

For each pixel, the entire THz waveform is recorded and averaged over four readings to reduce any fluctuations arising from the laser. The signal to noise ratio is approximately 1,000 to 1.

The impulse function is derived from the amplitude of the reflected radiation. In order to derive the input function for a particular pixel, two further measurements are made in addition to a measurement of the sample.

First, a baseline signal is measured. In the reflection measurement, it is important to try to reduce the effects of spurious reflections. The apparatus of FIG. 3 uses a Quartz window 67 through which the samples 61 and 63 are illuminated. Quartz window 67 has a lower interface 79 which will cause spurious reflections and also an upper interface 81 which will cause spurious reflections.

It is important to try to eliminate the effects of these two interfaces from the measurements. Therefore, prior to imaging the sample, a second Quartz window (not shown) is placed in the sample holder instead of sample 61 and 63. The amplitude of the detected THz signal is measured for each pixel so that a baseline signal is obtained through each pixel. Variations in Quartz window 67 and also variations in the incident angle of the irradiating radiation may cause artificial variations of the measurements of the sample. Therefore, the baseline is obtained for each pixel.

The baseline measurement was averaged twenty times to obtain baseline signal B(t).

A reference spectrum is also measured. This is measured by using the sample bolder with just Quartz window 67 on its own. This reference signal will be represented in the time domain as R(t).

First, in order to obtain an impulse function for one waveform, the baseline signal B(t) is subtracted from the measured time domain waveform S(t). This operation can be formed in either the time domain or frequency domain.

This baseline subtracted waveform should provide data where the spurious reflections due to the lower 79 and upper 81 interfaces of Quartz window 67 have been eliminated.

Next, the baseline subtracted waveform is complex Fourier transformed to give:

$$S'(v) - B'(v)$$

In order to use the reference signal, the baseline signal is again subtracted from the reference waveform R(t). This subtraction operation can be performed in either the time domain or the frequency domain. The result is then complex Fourier transformed to give:

$$R'(v) - B'(v)$$

The baseline subtracted measured data is then divided by the baseline subtracted reference signal in the frequency domain to give:

$$\frac{S'(v) - B'(v)}{R'(v) - B'(v)}$$

The data is then filtered. In general, a filter function will be described by F(t) and is complex Fourier transform will be represented by a F'(v).

A filter function preferably is used because the THz pulse system can generate and detect pulses comprising frequencies over some finite range, typically from less than 100 GHz to over 3 Thz. There is a high frequency limit above which the THz signal falls below the noise level of the detection system.

Similarly, the THz signal level falls below the noise level at low frequencies. Thus, there is a need to remove the high and low frequency noise. A particularly preferable function for achieving this is:

$$F(t) = \left| \frac{2}{\pi} \left\{ \frac{e^{-2(\frac{t}{\alpha})^2}}{\alpha} - \frac{e^{-2(\frac{t}{\beta})^2}}{\beta} \right\} \right|$$

The parameters $\alpha$ and $\beta$ are selected to control the high and low frequency roll-off of the function. $\alpha$ is set approximately the shortest THz pulse length (half cycle) obtainable within the THz system. $\beta$ is set to be much longer than the THz pulse. In operation, the two parameters are optimised manually by the operator to obtain the best compromise between bandwidth and noise.

As the above function comprises two Gaussian functions with similar areas but opposite signs, the above function ensures that the integral of the filter function for all time is zero.

If the value of $\beta$ is comparable to or greater than the total time-delay scan range, then an alternative function can be used:

$$F(t) = \left| \frac{2}{\pi} \left\{ \frac{e^{-2(\frac{t}{\alpha})^2}}{\alpha} - \frac{1}{T} \right\} \right|$$

where T represents the total range of delay times used i.e. $T = T_{max} - T_{min}$. This ensures that the overall integral from $T_{min}$ to $T_{max}$ is always zero.

The filter function is multiplied by the complex Fourier transform of the signal which is being corrected by the baseline and the reference.

Once the impulse function has been derived as illustrated in FIG. 4, the image is then generated using the analysis described with reference to FIG. 5.

Figure 5:
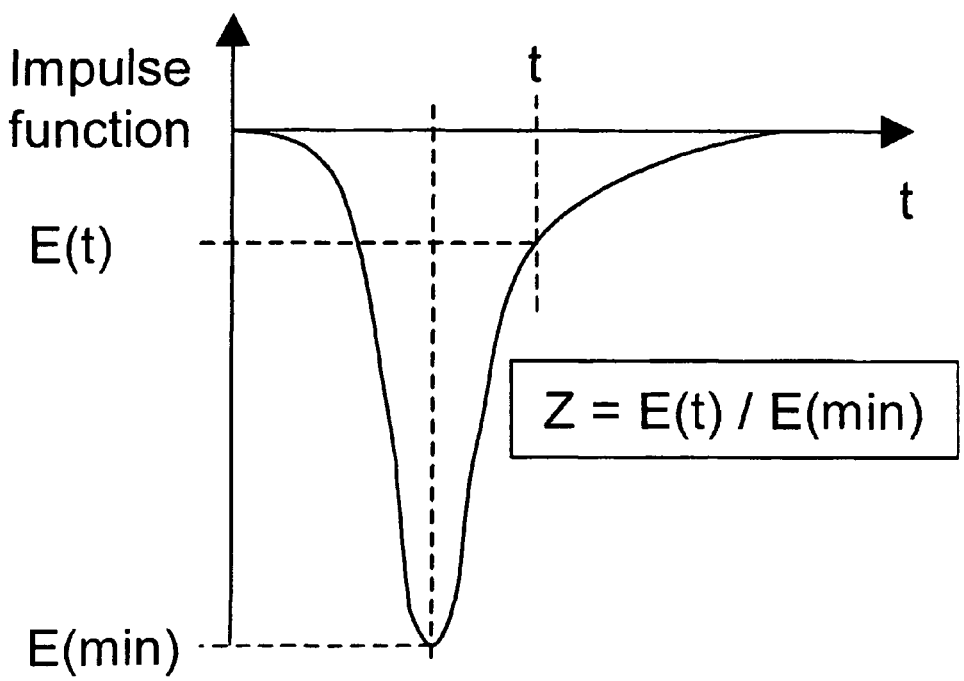
FIG. 5 is a schematic illustrating the analysis of an impulse function in accordance with an embodiment of the present invention.

FIG. 5 shows a schematic impulse function for just one pixel. In order to generate an image of the sample, it is important to derive a meaningful parameter from this trace which can be plotted for each pixel. By a meaningful parameter, we mean a parameter which can be used to indicate and emphasise variations in the sample.

The inventors have surprisingly found that the following method of deriving a parameter provides an image with a remarkable sharp contrast for illustrating a number of variations in the sample but has found to be of particular use for indicating the presence of Basal Cell Carcinoma.

The value of the impulse function at the minima is measured. Also, the value of the impulse function at a time t. In this example, the time t is chosen from the times which correspond to ascending values of the first parameter after the minima.

A parameter Z is derived by dividing the first parameter at a time t by the value of the first parameter at the minima i.e.

$$Z = \frac{E(t)}{E(min)}$$

To generate an image, each value of Z is assigned a colour and a full colour map is generated by plotting z on the z axis against x and y which define the pixel positions. As the contrast varies with the chosen value of t, t is chosen in order to give the best contrast. "t" is fixed for the image.

Figure 6:
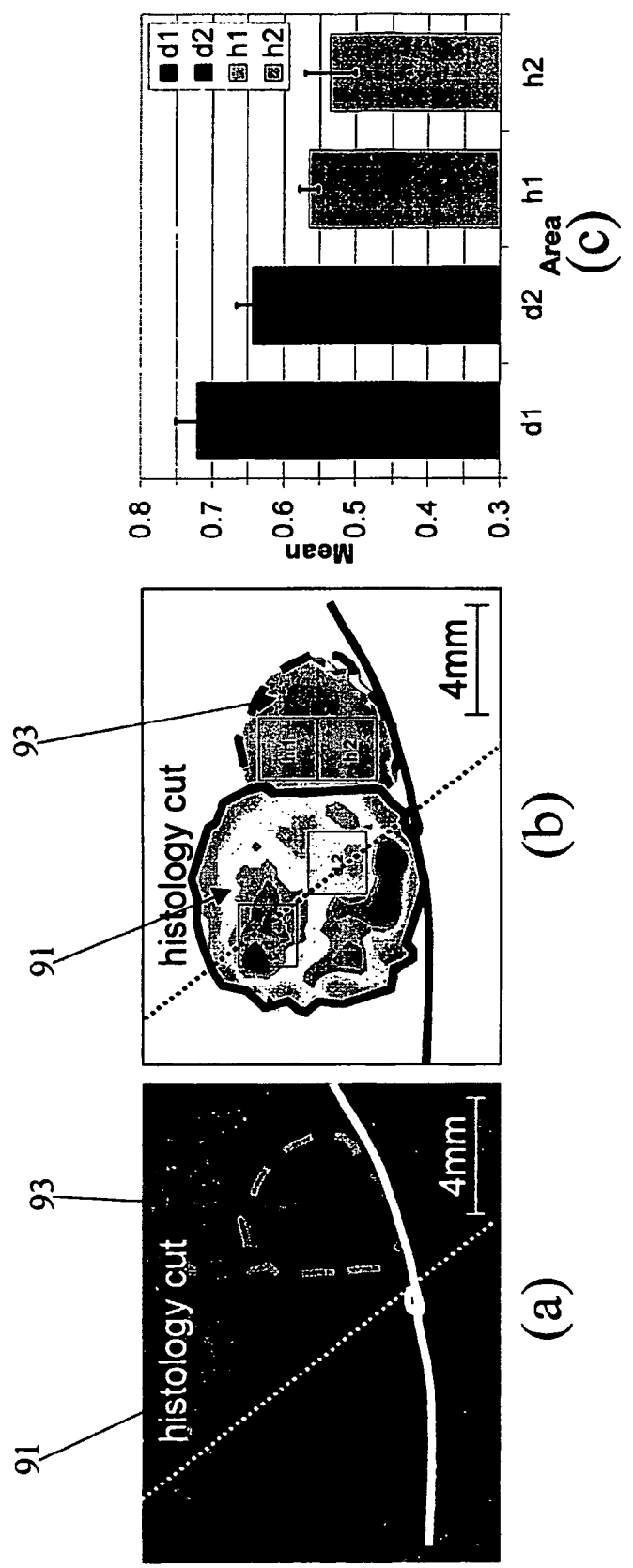
FIG. 6a illustrates a visible image of a skin tumour.
FIG. 6b illustrates a corresponding Terahertz image of the same sample produced in accordance with an embodiment of the present invention and FIG. 6c is a plot of the mean value of the THz signal of the image of FIG. 6b plotted for four pixels of the image.
Figure 7:
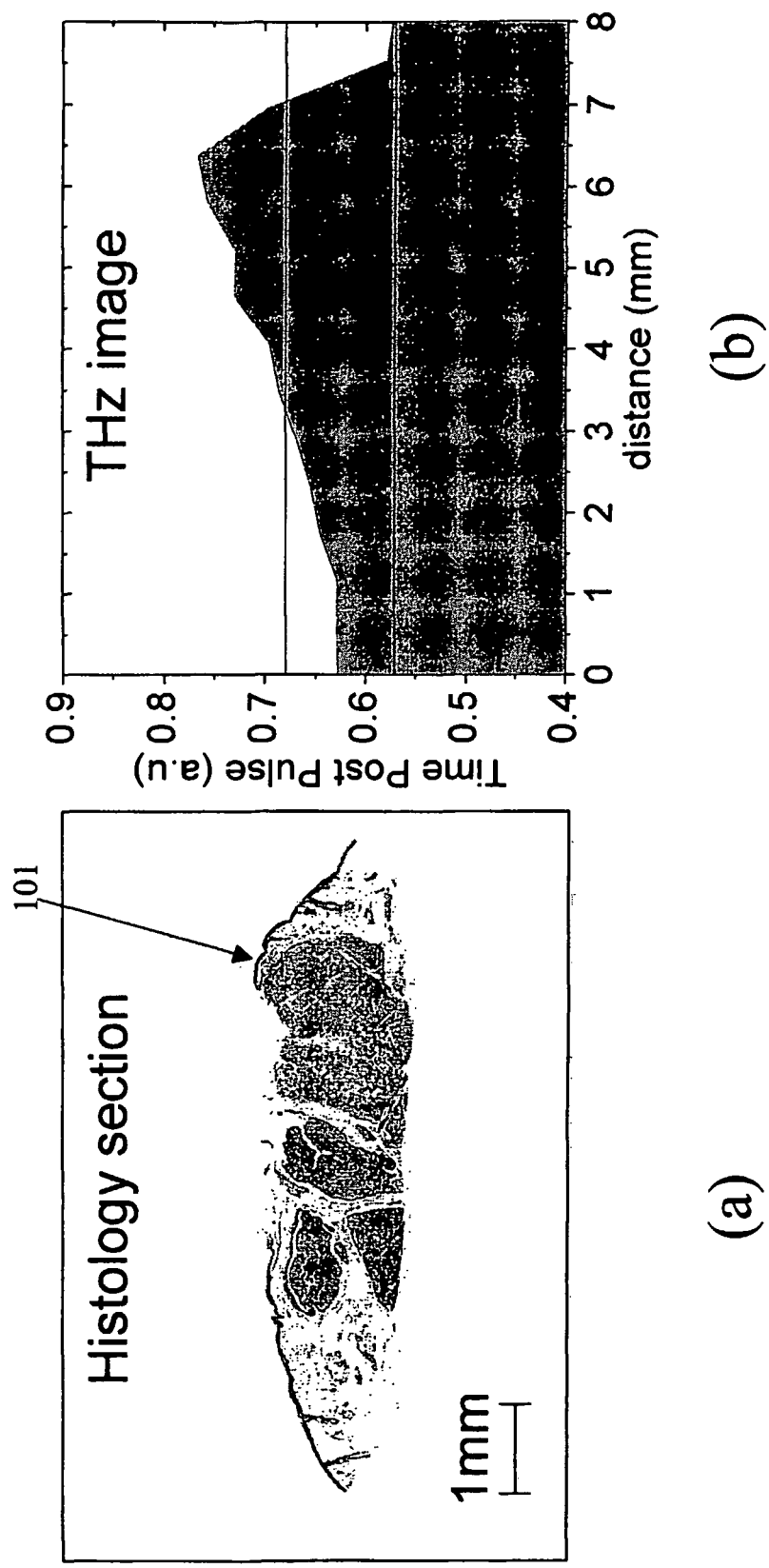
FIG. 7a is a vertical histology section of a skin tumour and FIG. 7b is a corresponding section through a Terahertz image obtained in accordance with an embodiment of the present invention.

FIG. 6a illustrates a visual image of a non-recurrent tumour present on a nasal tip. The tumour is 7 mm in diameter. The tumour 91 is shown on the left of the image with healthy tissue 93 shown on the front of the image. A histology cut is indicated on both diagrams 6a and 6b with a dotted line. The importance of this will be described with reference to FIG. 7.

The false colour THz image 6b shows a strong contrast between the diseased and healthy tissue. The healthy tissue 93 shows a fairly uniform greyscale contrast throughout. The strong contrast between the diseased and healthy tissue which is illustrated in FIG. 6b is not present in the visible image where it is difficult to differentiate between the two.

Four areas, d1, d2, h1 and h2 corresponding to two areas of diseased tissue and two areas of healthy tissue are indicated on FIG. 6b. FIG. 6c illustrates a plot of the main value of the impulse function for each of these areas. It can be seen that the mean value for the two diseased areas is much higher than that of the mean value for the two healthy areas. The standard derivation is used to illustrate an error bar for each of the regions. It can be seen that even in the worse case scenario, it is possible to clearly distinguish the diseased areas d1 and d2 from healthy areas h1 and h2.

A histological analysis of the sample was then performed. A vertical histology section was taken through the sample illustrated in FIGS. 6a and 6b along the dotted line. The results of which are indicated in FIGS. 7a and 7b.

In the histology section shown in FIG. 7a, the epidermis is shown as a thick line 101 of histology section 7a. It is noted that the epidermis is missing in the centre of the section. This is because the tissue is preferentially scraped prior to excision. As a result of increased vascularisation around the tumour site and the changing composition of the skin structure within this region, the epidermis is more delicate and susceptible to preferential bleeding in the surrounding healthy tissue. This effect is utilised by the surgeons in assisting identifying the location of the tumour. The tumour had not broken through to the surface before preferential scrapping.

Tumour shrinkage is due to desification, a result of the histological preparation process. The tumour is highly cellular and has a fibrous casing. The epidermis is pushed to one side by the tumour and as a result, thickened.

Turning to the THz image of FIG. 7b, the upper line indicated on the plot is the mean value for the diseased tissue. The lower line is the mean value for the healthy tissue. The THz image is taken in the same direction as that of the histology section. In other words, it is just a slice through the greyscale image of FIG. 6b taken along the dotted line. Towards the right hand side of the trace, diseased tissue is seen which corresponds to the histology section. Towards the left hand side of the trace, the healthy tissue is seen as shown in the histology section.

Figure 8:
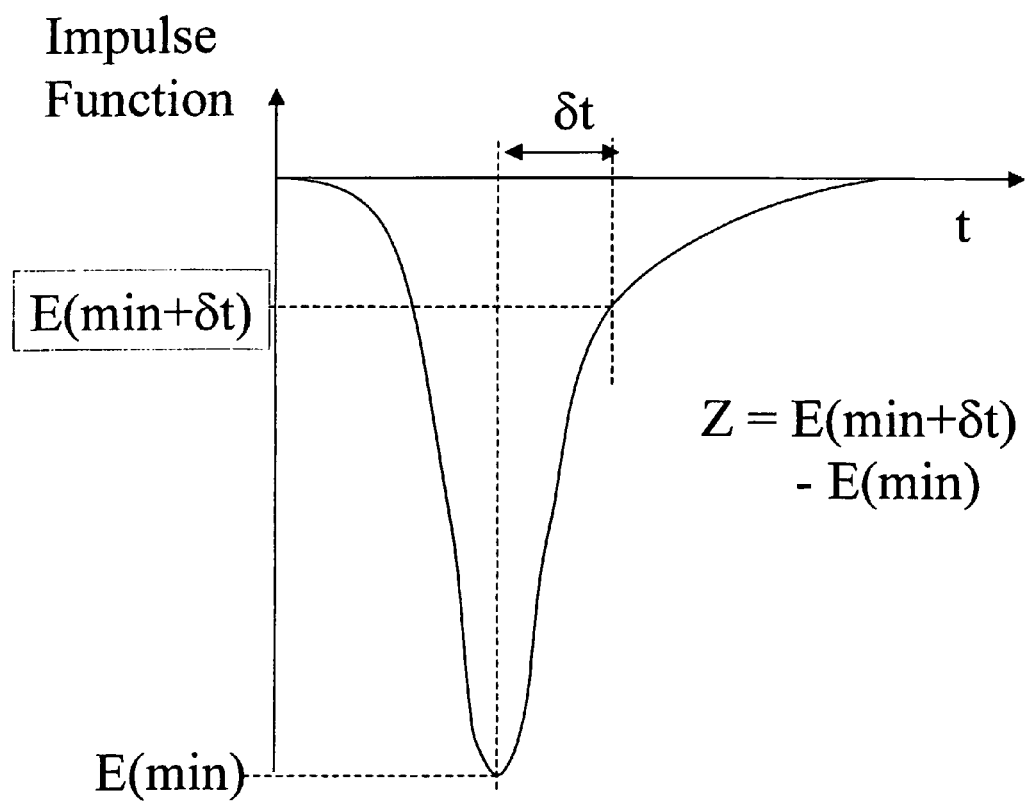
FIG. 8 is a schematic illustrating the analysis of an impulse function in accordance with a further embodiment of the present invention.

In the analysis technique shown in FIG. 8, the impulse function is derived in the same manner as that described with reference to FIG. 5. The parameter Z is then derived by subtracting the value of the first parameter at the minima from the value of the first parameter at an arbitrary time t which occurs at a time $\delta t$ after the minima i.e. $Z=E(min+\delta t)-E(min)$.

The minima may move in time from point to point across the sample. t is defined relative to E(min), thus t moves with the minima. To optimise the image, the parameter $\delta t$ is optimised as $\delta t$ is fixed for each image.

Figure 9:
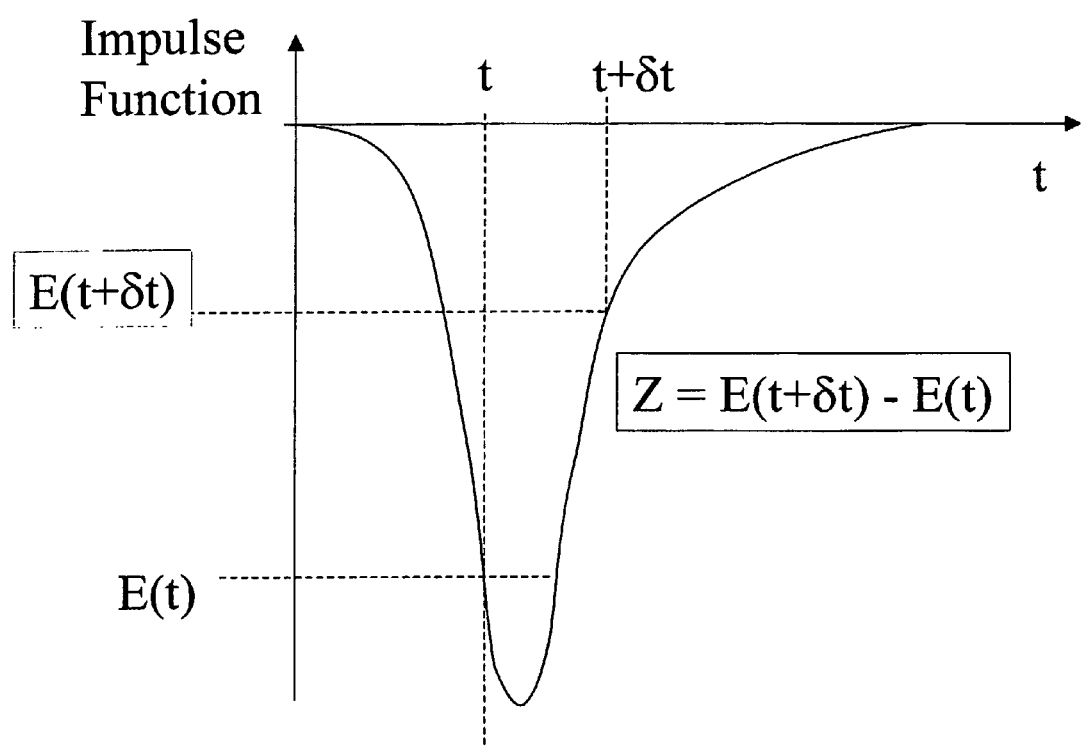
FIG. 9 is a schematic illustrating the analysis of an impulse function in accordance with a yet further embodiment of the present invention.

FIG. 9 shows a variation on the analysis technique described with reference to FIG. 8. Again, the impulse function is derived in the same manner as described with reference to FIG. 5.

The parameter Z is calculated by subtracting the value of the first parameter at a time $t_2$ from the value of the first parameter at time $t_1$ where $t_1=t_2+\delta t$. $t_2$ does not have to coincide with the minima. As shown in FIG. 9, $t_1$ and $t_2$ may lie on opposing sides of the minima or they may lie on the same side.

Again, as described with reference to FIG. 8, since $t_1$ is defined relative to $t_2$, $\delta t$ is optimised.

Figure 10:
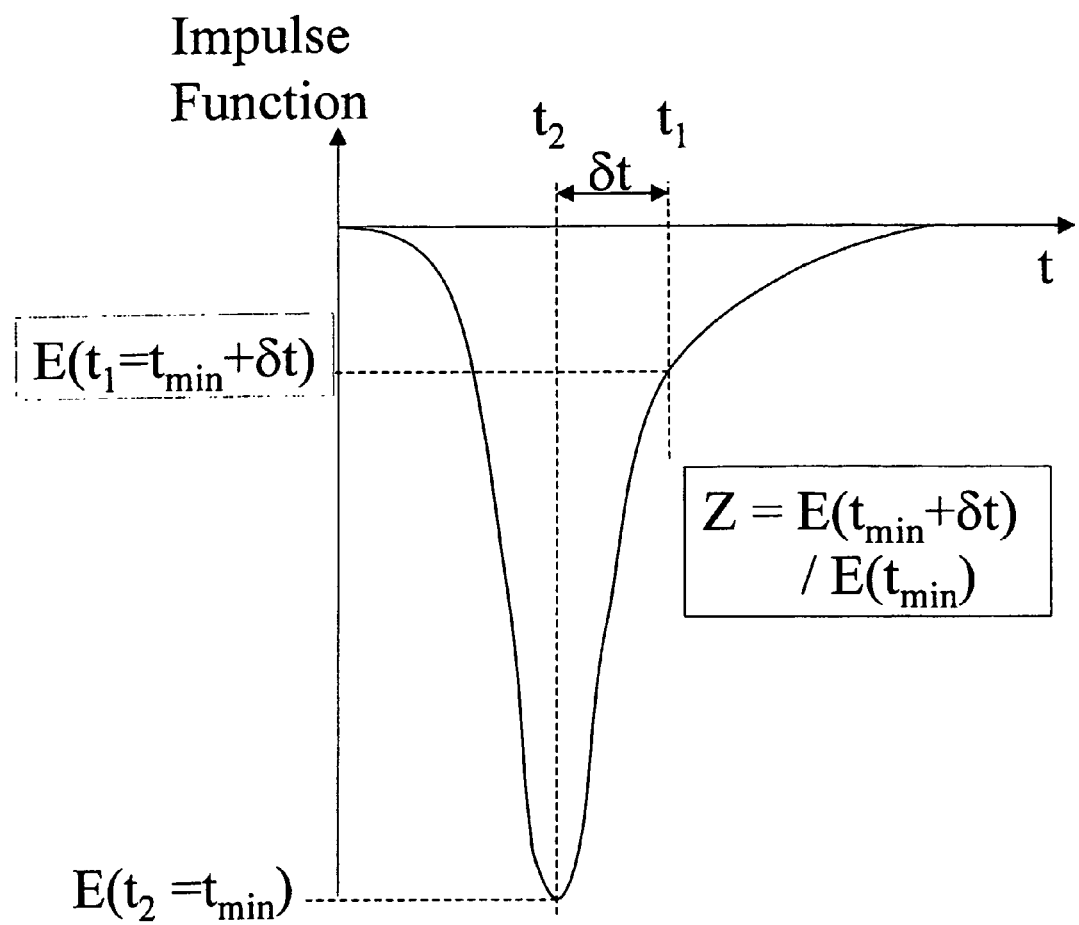
FIG. 10 is a schematic illustrating the analysis of an impulse function in accordance with an even further embodiment of the present invention.

FIG. 10 shows a yet further technique for deriving Z. Again, as described with reference to FIG. 5, the impulse function is derived as a function of time. Z is then calculated by dividing the value of the first parameter at a time t which equals $t_{min}+\delta t$ divided by the value of the first parameter at the minima. In other words:

$$Z = \frac{E(min+\delta t)}{E(min)}$$

This technique is similar to that described in relation to FIG. 5. However, in the analysis technique of FIG. 5, $t_1$ is fixed across a single image. If the minima moves (and hence $t_2$ moves from pixel to pixel) $t_1$ still remains fixed. In the analysis technique described with reference to FIG. 10, $t_1$ is defined in relation to $t_2$, thus $t_1$ moves with $t_2$ and $\delta t$ is fixed for a particular image.

As mentioned with reference to FIGS. 5, 8, 9 and 10, careful selection of t enhance the contrast. Generally, the operator of such equipment will be able to scan through a number of images at different t in order to obtain the best contrast. Such an apparatus for performing this is illustrated in FIG. 11.

Figure 11:
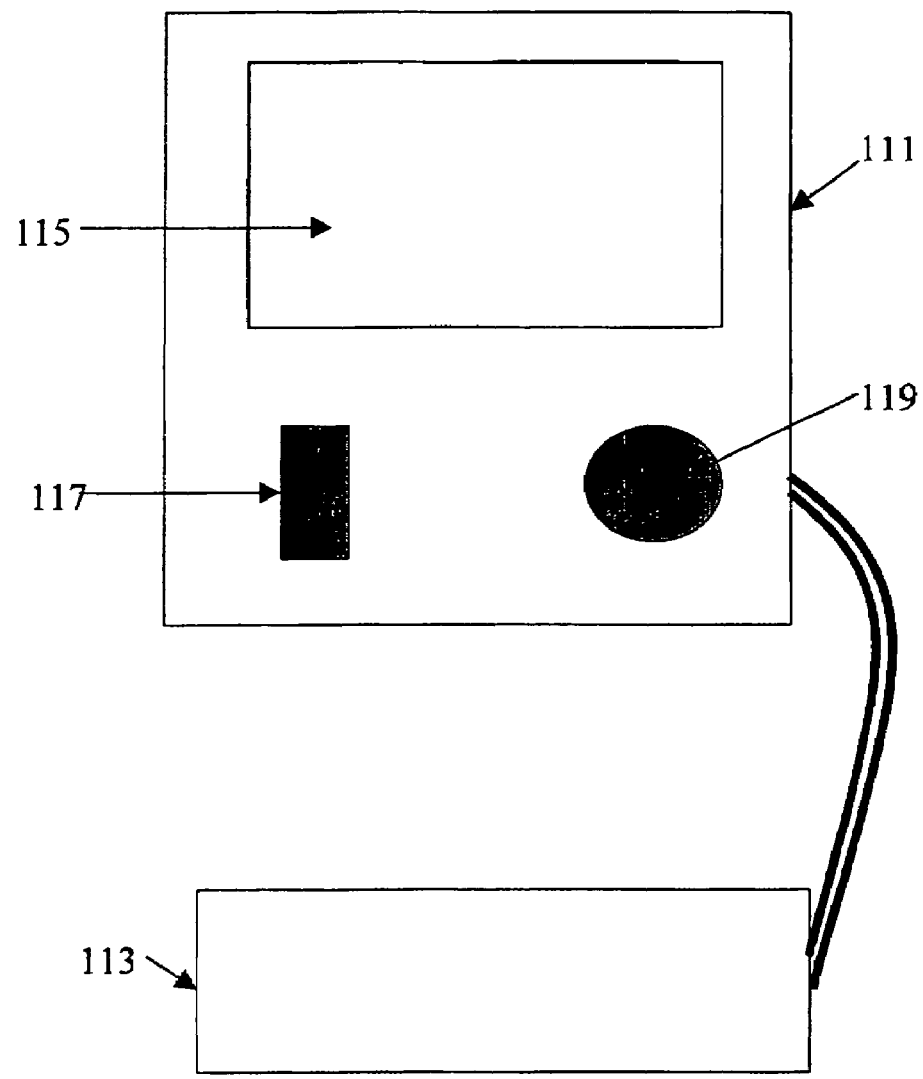
FIG. 11 is an apparatus which can optimise the contrast of a THz image in accordance with an embodiment of the present invention.

FIG. 11 shows a schematic view of such a system. The system comprises a controller 111, a THz imaging system 113. The THz imaging system is of the type described with reference to either of FIGS. 1 and 2. To avoid unnecessary repetition, details of it will not be repeated here and the whole system will be represented by box 113. Controller 111 has a screen 115 which the operator can use to view a false colour THz image of the sample under test as explained with reference to FIGS. 4 and 5 and as illustrated in FIG. 6b. The controller 111 has two modes of operation. A set-up mode and a fixed imaging mode. The controller switches between these two modes using switch 117.

In the set-up mode, the full THz spectrum and hence impulse function is derived for each pixel of the sample. The image is then derived by calculating Z for a given t. t may be a fixed value for all pixels or may be fixed from a second time value which may correspond to a physical feature of the data set. The user can then turn dialler 119 and watch the contrast of the image displayed on screen 115 change as t or $\delta t$ is varied. The operator can thus choose an optimum value of t or $\delta t$.

Alternatively, the controller itself may be provided with its own means for determining the optimum contrast as a function of t. For example, the controller can calculate the mean value of Z for each pixel and choose a value of t where the variation in Z is at its largest. Alternatively, more complex statistical techniques may be employed where only representative values of the impulse function are considered in determining the best contrast.

Once the operator or controller itself 111 has determined the best contrast, the operator can then switch 117 to switch the controller 111 onto fixed mode. In this fixed mode, the controller will instruct imaging apparatus 113 to only take data at the minima and at the preferred value of t. This technique substantially reduces the acquisition time for the image. Once t has been determined for a sample, it can be used for that whole sample. It has also been found that the cell value of t can be used as samples of the same type. For example, for samples which are Basal Cell Carcinoma, the operator would expect to use the same value of t.

Controller 111 can be pre-programmed with t values which are known to provide optimum contrast for certain samples. Alternatively, controller 111 may be provided with a look-up table such that the operator can enter the type of sample which is to imaged and the controller can automatically select the correct t or δt value.

Figure 12:
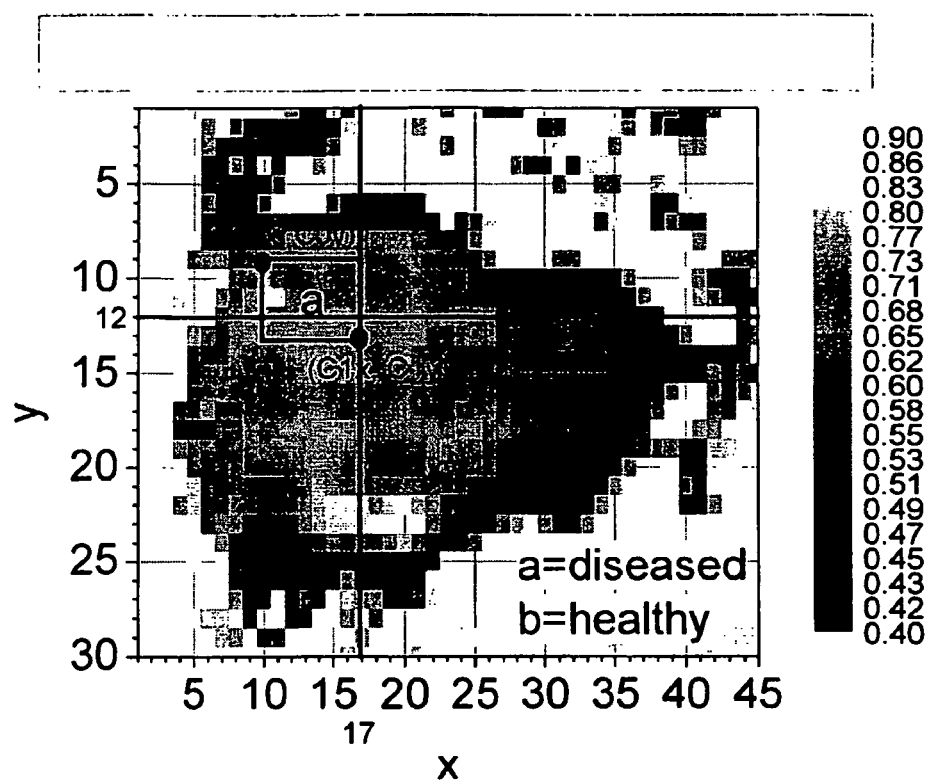
FIG. 12 is an image of a tumour generated using E(t)/E(min) as explained with reference to FIG. 5.

FIG. 12 illustrates an image of a skin tumour obtained by dividing the magnitude of the impulse function at a time t=1098 (arbitrary units) with the impulse function at the minima of the electric field. This is explained in detail with reference to FIG. 5. Specifically, the value of E(t)/E(min) for t=1098 is plotted for each pixel to produce the image.

This figure will now be used to explain how the image may be optimised. Two areas "a" and "b" are selected from the image. Area "a" is believed to represent diseased tissue whereas area "b" is believed to represent healthy tissue.

Figure 13:
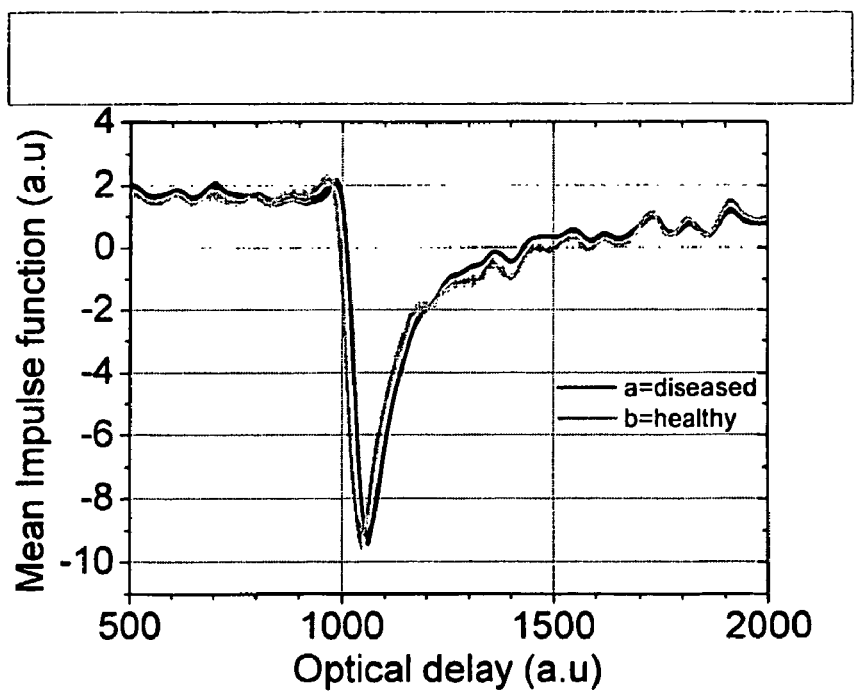
FIG. 13 illustrates two time domain spectra averaged over areas "a" and "b" of FIG. 12.

The mean impulse function for both areas "a" and "b" is plotted for each time point as shown in FIG. 13. Formally, for area "a", the function:

$$\overline{E}_a(t)$$

is plotted where $$\overline{E}_a(t) = \frac{\sum_i^n E_i(t)}{n}$$

E being the impulse function and n being the number of pixels in area "a". The mean impulse function for area "b" is calculated in the same manner and plotted.

The width of the curves represents the standard deviation since the waveform is calculated over an area.

These two waveforms are then compared in order to determine the time values where a plot of E(t) will produce an image with the best contrast between areas "a" and "b".

Figure 14:
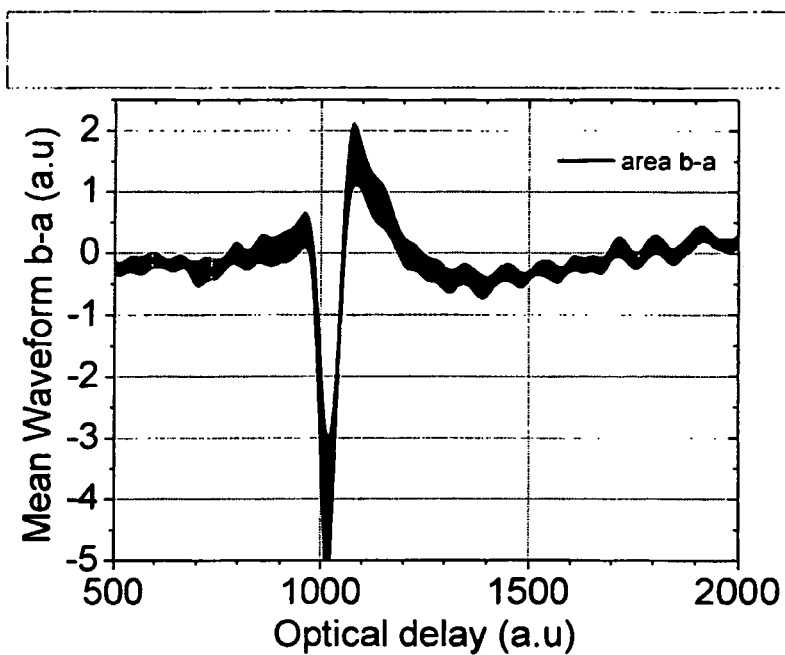
FIG. 14 illustrates a spectra derived from the difference between the two spectra of FIG. 13.

FIG. 14 illustrates the case where the spectra for the diseased tissue is subtracted from the waveform for the healthy tissue. It can be seen that the largest difference between these two waveforms occurs close to t=1100. Thus, indicating that an image produced using this value of "t" as the first time value will produce good contrast. For example, the image may be produced by plotting E(t), E(t)/E(min), E(t)−E(min) etc.

Figure 15:
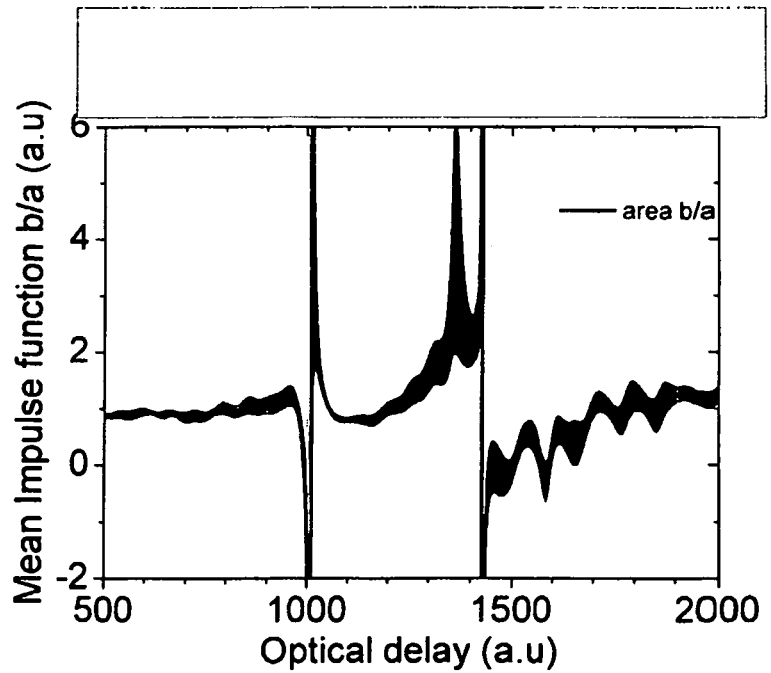
FIG. 15 illustrates a spectra derived by dividing one spectra of FIG. 13 by the other spectra of FIG. 13.

FIG. 15 illustrates the case where the two waveforms are compared by dividing the waveform for healthy tissue with that from diseased tissue. This comparison method also allows a value of "t" to be determined which can be used as the first time value.

Figure 16:
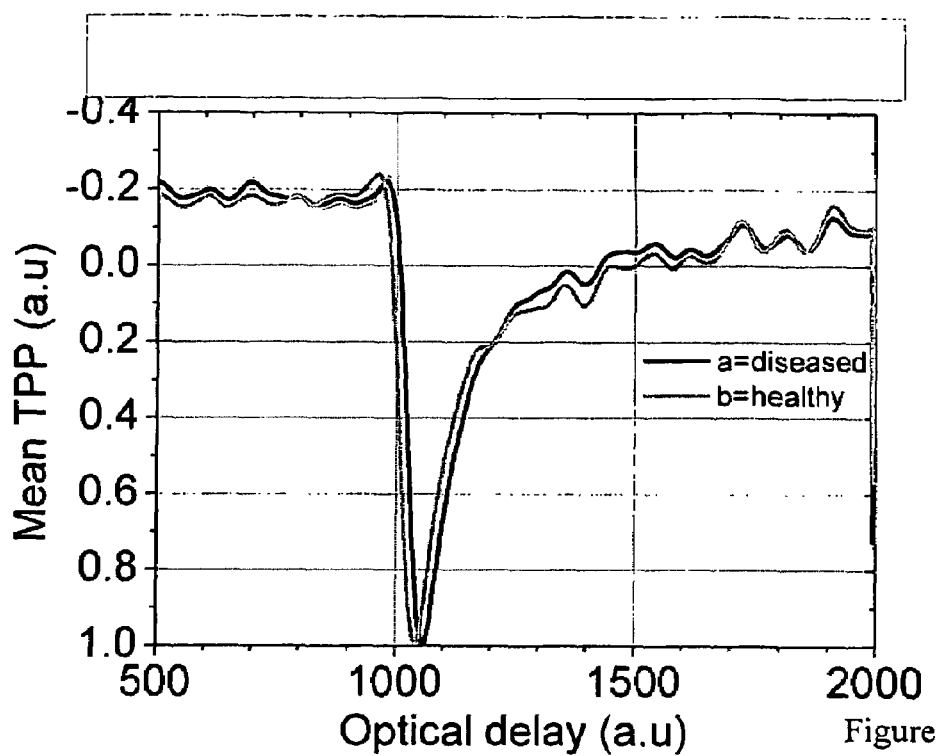
FIG. 16 illustrates a plot of two time domain spectra derived by plotting E(t)/E(min), the spectra are similar to those of FIG. 13 but have been normalised to the value E(min)

In FIG. 13 the mean impulse function was derived for two areas and used to determine an optimum value of "t". In FIG. 16, the mean impulse functions of FIG. 13 are normalised to the value $E_{min}$, formally:

$$\frac{\overline{E}_a(t)}{E_{min}}$$

is plotted, where:

$$\overline{E}_a(t) = \frac{\sum_i^n E_i(t)}{n}$$

E being the impulse function and n being the number of pixels in area a. The normalised mean impulse function for area 'b is calculated in the same manner and plotted.

Figure 17:
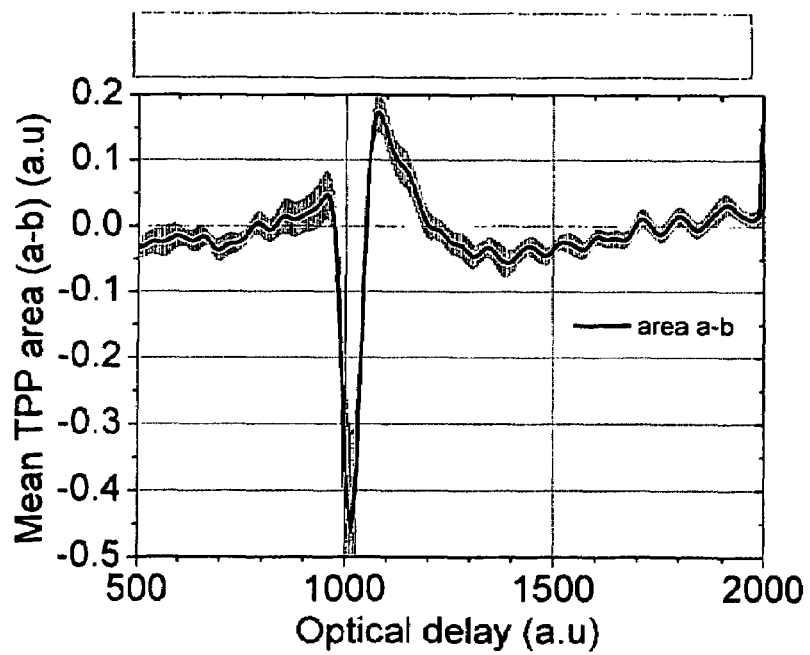
FIG. 17 illustrates a time domain spectra derived from the difference of the two spectra of FIG. 16.
Figure 18:
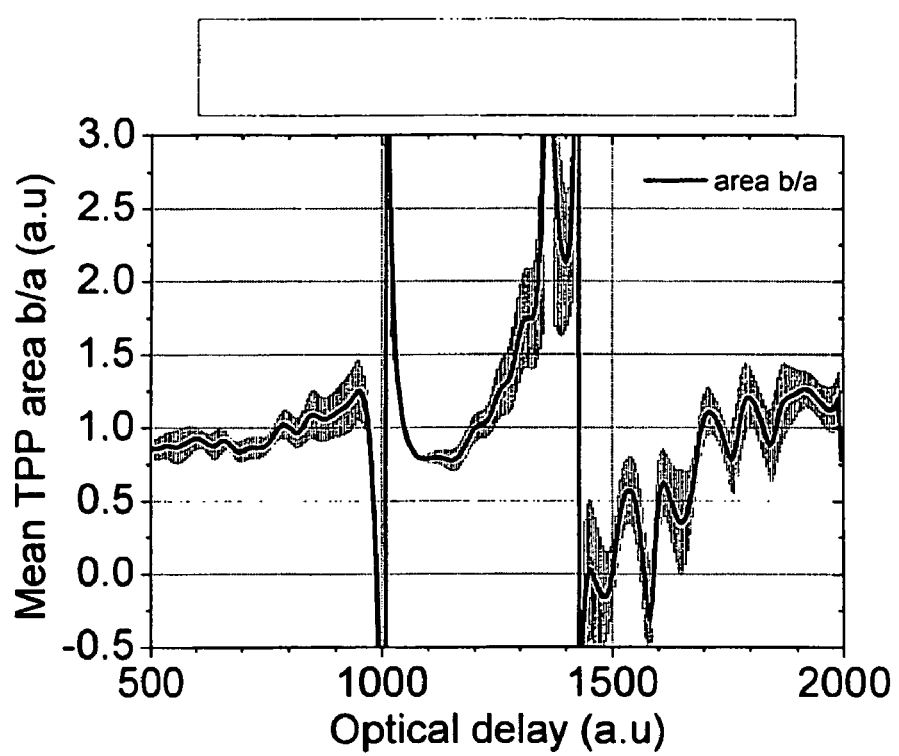
FIG. 18 illustrates a time domain spectra derived from dividing one spectra of FIG. 16 by the other spectra of FIG. 16.

FIG. 17 illustrates the spectra of FIG. 16 subtracted from one another whereas FIG. 18 illustrates the spectra from FIG. 16 divided by one another.

In the same manner as described with reference to FIGS. 14 and 15, values of "t" may be derived from the spectra of FIGS. 17 and 18 which produce an image with good contrast.

The present invention may also be used to compare three different types of tissue within the sample and different t values may be selected to identify different types of tissue.

Figure 19:
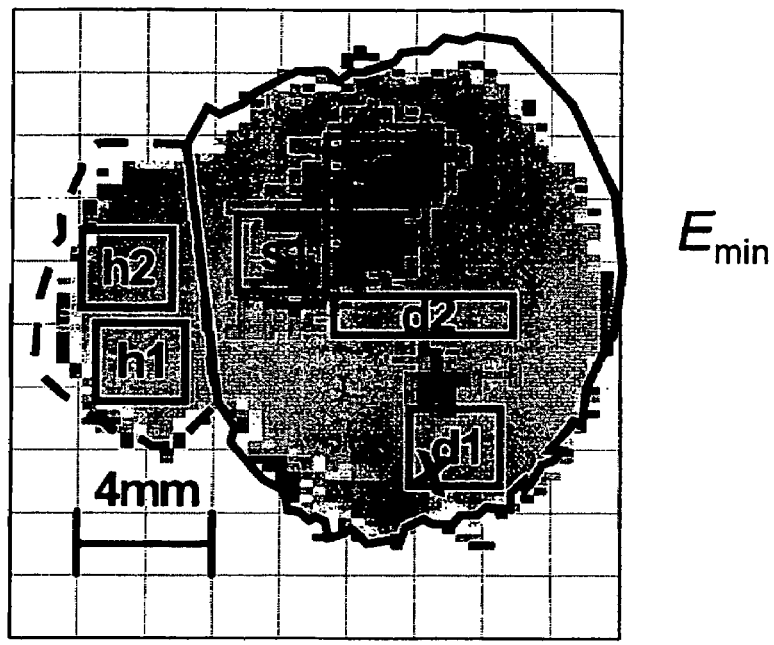
FIG. 19 illustrates an image of a tumour derived by plotting the magnitude of the main minima of the impulse function for each pixel in the x and y direction.

In FIG. 19, six areas are selected, h1 and h2 which represent healthy tissue, s1 and s2 which represent inflamed tissue and d1 and d2 which represent diseased tissue.

The image of FIG. 19 is generated by plotting the minima of the impulse function for each pixel in the x and y directions i.e. Emin is plotted. The minimum mean impulse function for each of these areas, averaged across each area, is then plotted and the graph shown in FIG. 20. The vertical error bars represent the standard deviation.

FIG. 21 illustrates the mean impulse function E(t) for healthy tissue (calculated from areas h1, h2), inflamed tissue (calculated from areas s1 and s2) and diseased tissue (calculated from areas d1 and d2) derived from the sample illustrated in FIG. 19. FIG. 22 illustrates the spectra of FIG. 21 which has been normalised to the value of $E_{min}$ i.e E(t)/E(min). The width of the spectra represents the standard deviation.

Figure 20:
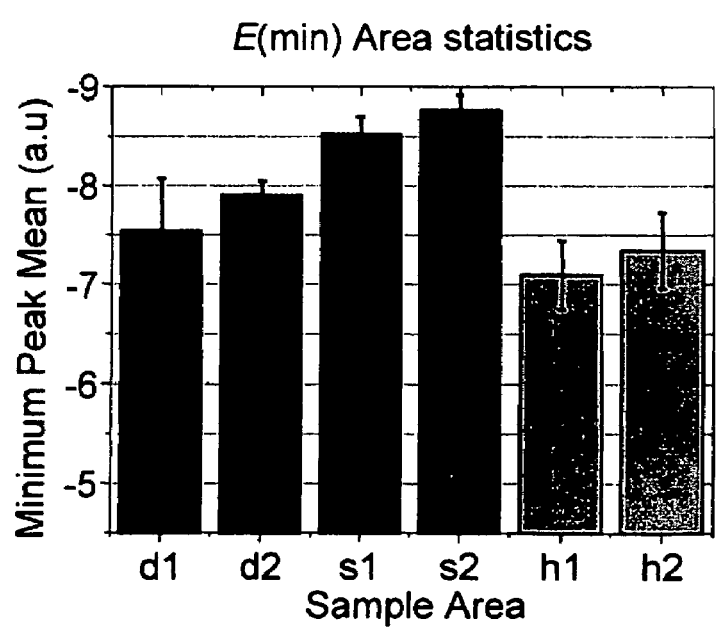
FIG. 20 illustrates the mean value of the minimum view averaged over each of the areas s1, s2, d1, d2, h1 and h2 indicated in FIG. 19.

It can be seen by viewing FIGS. 20 and 21 side by side that the shape of the waveforms change between a plot of mean E(t) and mean $E(t)/E_{min}$. The changes between these two waveforms may be used to distinguish between different tissue types.

FIGS. 23 and 24, illustrate in detail the region between t=0.8 ps and t=1.6 ps for FIGS. 21 and 22 respectively. In FIG. 23, it can be seen that there is little difference between the curves for the diseased and inflamed tissue which just start to deviate from one another at about t=1.1 ps. However, the spectra which represents healthy tissue is clearly separated from the spectra from both diseased and inflamed tissue over the whole of the selected time range.

In FIG. 24, the spectra from the healthy and inflamed tissue is seen to follow a similar trajectory whereas the spectra from the diseased tissue follows a lower path which is well separated from the other two spectra.

The time value of 1.2 ps is clearly marked on both FIGS. 23 and 24. Generating an image by plotting E(t=1.2 ps) can thus be used to clearly distinguish between healthy tissue on the one hand and diseased and inflamed tissue on the other.

Generating an image by plotting $E(t=1.2 \text{ ps})/E_{min}$ can be used to clearly distinguish between diseased tissue on the one hand and health and inflamed tissue on the other.

By choosing a different time value, it is possible to distinguish between diseased and inflamed tissue. FIGS. 25 and 26 are identical to FIGS. 21 and 22, but are repeated in order to allow comparison with FIGS. 27 and 28. FIGS. 27 and 28 show a detail of the plots of FIGS. 25 and 26 between 1 ps and 6 ps.

In FIG. 27, the diseased tissue trace lies well below that of the traces for healthy tissue and inflamed tissue which follow a similar path. However, in FIG. 28, where $E(t)/E_{min}$ is plotted, a clear distinction can be seen between the three traces, the diseases tissue trace being the lowest trace, the healthy tissue trace being the middle trace and the upper trace corresponding to inflamed tissue.

Thus, an image formed by plotting $E(t=3.7 \text{ ps})$ can be used to distinguish between diseased tissue on the one hand and healthy and inflamed tissue on the other, whereas an image formed by plotting E(t)/E(min) where t=3.7 ps can be used to distinguish between diseased tissue, healthy tissue and inflamed tissue.

When it is desirable to distinguish between three different tissue types, it is necessary to chose a time value which emphasises the difference between all three tissue types and not just two tissue types.

Figure 29:
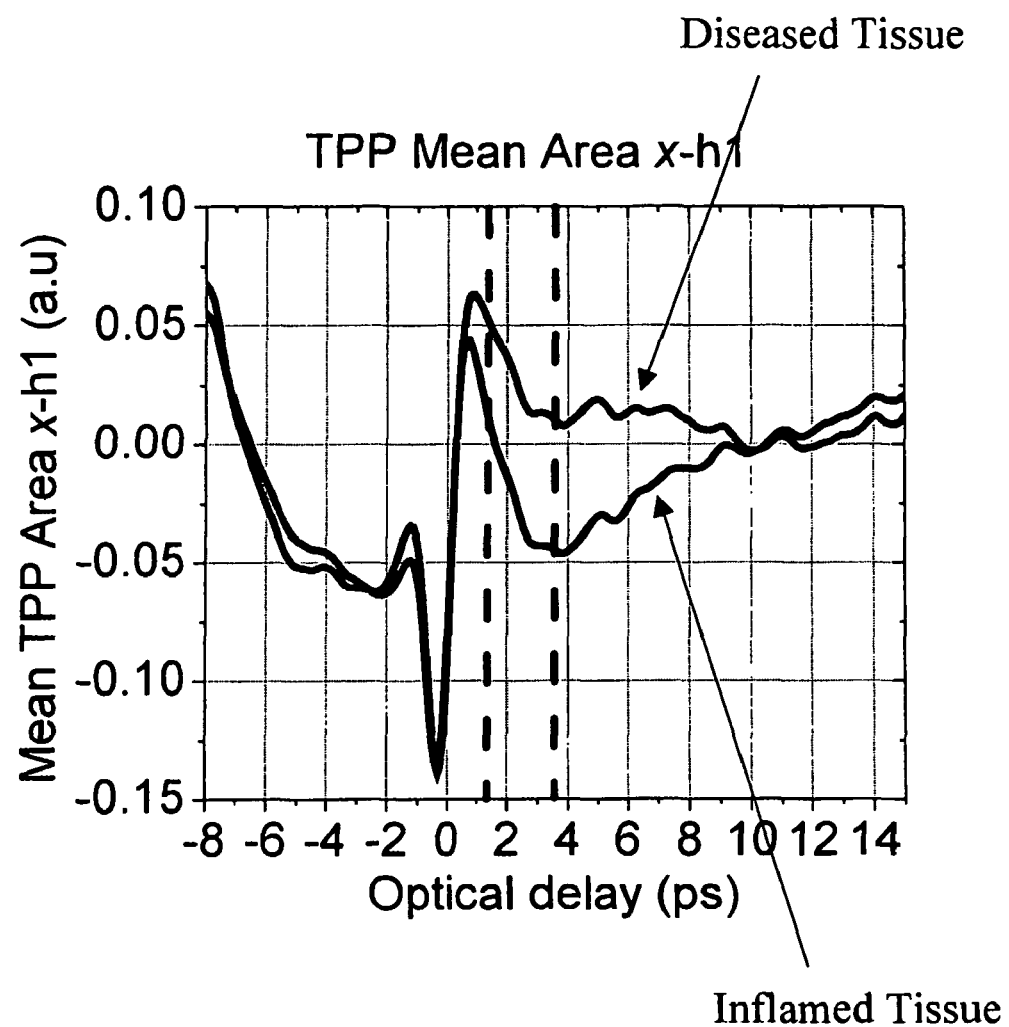
FIG. 29 illustrates a spectra of two time domain spectra, the upper spectra being produced by subtracting the spectra obtained from area h1 in FIG. 19 from the spectra obtained from the diseased tissue areas d1 and d2; the lower plot is a spectra obtained by subtracting a mean spectra obtained from healthy tissue area h1 of FIG. 19 from inflamed tissue areas s1 and s2.

FIG. 29 illustrates two spectra. The upper spectra is produced by subtracting the spectra formed by calculating $E(t)/E_{min}$ for healthy tissue from the spectra formed by calculating $E(t)/E_{min}$ for diseased tissue. The lower spectra is produced by subtracting the spectra formed by calculating $E(t)/E_{min}$ for healthy tissue from the spectra formed by calculating $E(t)/E_{min}$ for inflamed tissue.

In order to produce an image which clearly shows contrast between healthy and diseased tissue, a time value should be chosen where the magnitude of the upper spectra is greatest. To produce an image which clearly shows contrast between healthy and inflamed tissue, a time value should be chosen where the magnitude of the lower spectra is greatest. However, in order to distinguish between diseased and inflamed tissue, it is necessary to choose points where the difference between the two spectra is also large.

For example, in FIG. 29, both traces show a large negative value at about 0.7 ps. However, although taking this value of t will produce an image where there is good contrast between healthy tissue and diseased tissue and between healthy tissue and inflamed tissue, such an image is unlikely to show contrast between diseased tissue and inflamed tissue. However, producing an image of $E(t)/E_{min}$ for t=3.7 ps or t=1.2 ps will show good contrast between all three tissue types.

Figure 30:
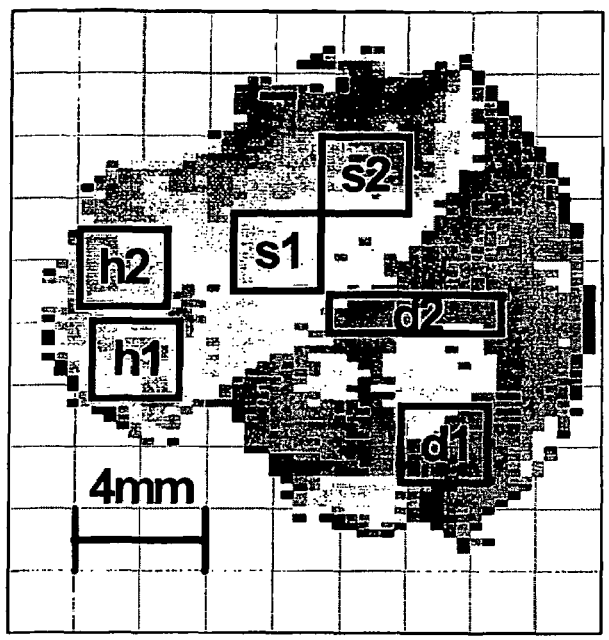
FIG. 30 illustrates an enhanced image obtained by plotting the parameter E(t)/E(min) for t=1.2 picoseconds.
Figure 31:
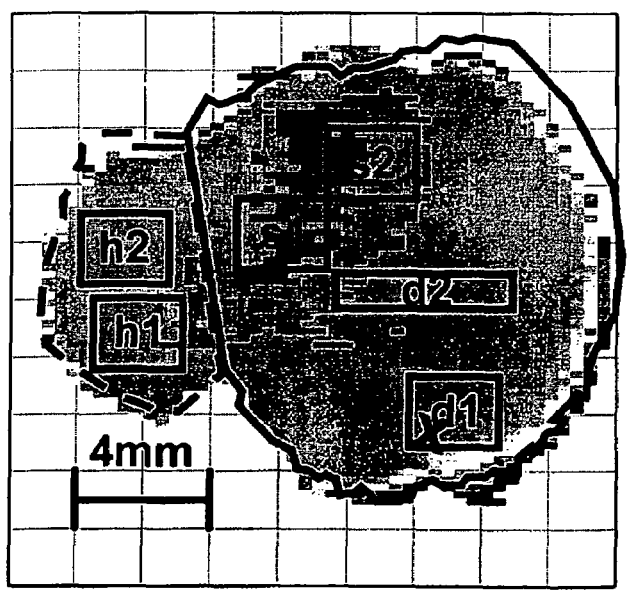
FIG. 31 illustrates an image obtained by plotting E(t)/E(min) for t=3.7 picoseconds.

FIGS. 30 and 31 illustrate images produced by plotting $E(t)/E_{min}$ for each pixel for t=1.2 ps (FIG. 30) and t=3.7 ps (FIG. 31).

The invention claimed is:

1. A method of imaging a sample, the method comprising:
   (a) irradiating a sample with a pulse of electromagnetic radiation, said pulse having a plurality of frequencies in the range from 25 GHz to 100 THz;
   (b) determining a first parameter at least related to the amplitude of the radiation, which is either reflected from and/or transmitted by the sample, in the time domain;
   (c) calculating the value of the first parameter at a first time value relative to the value of the first parameter at a second time value, wherein the second time value coincides with a physical feature of the first parameter with respect to time; and
   (d) generating an image of the sample by plotting the value of the first parameter calculated in step (c) for different spatial points over an area of the sample.

2. A method according to claim 1, wherein said physical feature is a predetermined maxima or minima of the first parameter with respect to time.

3. A method according to claim 1, wherein step (c) comprises the step of subtracting the value of the first parameter at the second time value from the value of the first parameter at the first time value and step (d) comprises plotting the value of the first parameter at the second time value subtracted from the value of the first parameter at the first time value for different spatial points over an area of the sample.

4. A method according to claim 1, wherein in step (c), the first time value is one of the values, ascending or descending, to or from, a local minima or maxima and said second time value coincides with said local minima or maxima, and wherein the first time value does not coincide with a local maxima or minima.

5. A method according to claim 4, wherein step (c) comprises the step of choosing the second value to correspond to a predetermined minima of the first parameter and the first time value is chosen from the subsequent time values ascending from the said minima.

6. A method according to claim 1, wherein the first time value is fixed in time for each point of the sample used to create a single image.

7. A method according to claim 6, further comprising the step of determining the first parameter for a plurality of first time values relative to the first parameter for the second time value for each point, the method further comprising the step of generating a plurality of images of the sample corresponding to each of the said first time values.

8. A method according to claim 7, further comprising the step of selecting the optimum first time value by selecting the image which provides the best contrast.

9. A method according to claim 1, wherein the first time value is a fixed time interval from the second time value for each part of the sample used to create a single image.

10. A method according to claim 9, further comprising the step of determining the first parameter for a plurality of different time intervals relative to the second time value for each part, the method further comprising the step of generating a plurality of images of the sample corresponding to each of different time intervals.

11. A method according to claim 10, further comprising the step of selecting the optimum time interval by selecting the image which provides the best contrast.

12. A method according to claim 1, further comprising the steps of:
   (i) selecting n regions of said sample, where n is an integer of at least 2;
   (ii) producing n time domain spectra of a second parameter which is at least related to the amplitude of the radiation reflected from and/or transmitted by the sample, where the nth spectra is obtained by averaging the second parameter across the nth region and plotting this averaged value, as it varies with delay time;
   (iii) determining the first time value by comparing at least two of the n spectra derived in step (ii).

13. A method according to claim 1, wherein the first parameter is the amplitude of the radiation.

14. A method according to claim 1, wherein step (a) comprises:
irradiating the sample through a member which is transparent to the irradiating radiation and which abuts the sample,
the method further comprising the step of:
obtaining a baseline signal by irradiating the member in the absence of the sample and detecting the amplitude of the reflected radiation, and
wherein in step (b):
the first parameter is determined by subtracting the baseline signal from the detected amplitude of the radiation reflected from both the member and the sample.

15. A method according to claim 14, wherein the baseline signal is subtracted from the detected reflected radiation in the time domain.

16. A method according to claim 14, wherein step (b) comprises determining the first parameter by subtracting the baseline signal from the detected radiation from the sample and multiplying the baseline subtracted sample signal in the frequency domain by the complex Fourier transform of the function F(t), where F(t) is a non-zero function whose integral between time limits $t_a$ and $t_b$ is zero, and where $t_a$ and $t_b$ are chosen to encompass the part of interest of the reflected or transmitted pulse.

17. A method according to claim 1, wherein step (a) comprises:
irradiating the sample through a member which is transparent to the irradiating radiation and which abuts the sample,
the method further comprises:
obtaining a baseline signal by irradiating the member in the absence of the sample and detecting the amplitude of the reflected radiation, and
replacing the sample with a reference object of known reflectance and measuring a reference signal by measuring the amplitude of radiation reflected from the reference object,
wherein in step (b) comprises:
determining the first parameter by subtracting the baseline signal from the detected radiation and dividing the result by the reference signal in the frequency domain.

18. A method according to claim 17, wherein step (b) comprises determining the first parameter by subtracting the baseline signal from the amplitude of the detected radiation and dividing the result by the reference signal in the frequency domain and multiplying by the complex Fourier transform of the function F(t) in the frequency domain, where F(t) is a non-zero function whose integral between time limits $t_a$ and $t_b$ is zero, and where $t_a$ and $t_b$ are chosen to encompass the part of interest of the reflected or transmitted pulse.

19. A method according to claim 1, further comprising the step of:
replacing the sample with a reference object of known reflectance and measuring a reference signal by measuring the amplitude of radiation reflected from the reference object, and
wherein step (b) comprises:
determining the first parameter by dividing the detected amplitude with the reference signal in the frequency domain.

20. A method according to claim 19, wherein step (b) comprises determining the first parameter by dividing the amplitude of the detected radiation from the sample by the reference signal in the frequency domain and multiplying the result by the complex Fourier transform of F(t) in the frequency domain, where F(t) is a non-zero function whose integral between time limits $t_a$ and $t_b$ is zero, and where $t_a$ and $t_b$ are chosen to encompass the part of interest of the reflected or transmitted pulse.

21. A method according to claim 19, where:

$$F(t) = \left| \frac{2}{\pi} \left\{ \frac{e^{-2(\frac{t}{\alpha})^2}}{\alpha} - \frac{1}{T} \right\} \right|$$

and wherein α is a constant which is substantially equal to the shortest pulse length of the beam and T is substantially equal to the time which it takes the beam of radiation to penetrate to the deepest point of interest in the sample.

22. A method according to claim 1, wherein step (b) further comprises:
determining the first parameter by multiplying the amplitude of the detected radiation in the frequency domain by the complex Fourier Transform of function F(t), where F(t) is a non-zero function whose integral between time limits $t_a$ and $t_b$ is zero, and where $t_a$ and $t_b$ are chosen to encompass the part of interest of the reflected or transmitted radiation pulse.

23. A method according to claim 22, where $$F(t) = \left| \frac{2}{\pi} \left\{ \frac{e^{-2(\frac{t}{\alpha})^2}}{\alpha} - \frac{e^{-2(\frac{t}{\beta})^2}}{\beta} \right\} \right|$$

and α and γ are constants.

24. A method according to claim 22, wherein a is substantially equal to the shortest pulse length of the beam of pulsed radiation and b is set to be longer than the pulse length.

25. An apparatus according to claim 24, further comprising:
(i) means for selecting n regions of said sample, where n is an integer of at least 2;
(ii) means for producing n time domain spectra of a second parameter which is at least related to the amplitude of the radiation reflected from and/or transmitted by the sample, where the nth spectra is obtained by averaging the second parameter across the nth region and plotting this averaged value as it varies with delay time; and
(iii) means determining the first time value by comparing at least two of the n spectra.

26. A method of imaging a sample, the method comprising:
(a) irradiating a sample with a pulse of electromagnetic radiation, said pulse having a plurality of frequencies in the range from 25 GHz to 100 THz;
(b) determining a first parameter at least related to the amplitude of the radiation, which is either reflected from and/or transmitted by the sample, in the time domain;
(c) calculating the value of the first parameter at a first time value relative to the value of the first parameter at a second time value, wherein the second time value coincides with a physical feature of the first parameter with respect to time, by dividing the value of the first parameter at the first time value with the value of the first parameter at the second time value; and (d) generating an image by plotting the value calculated in step (c) for different points of the sample.

27. A method of imaging a sample, the method comprising:
 (a) irradiating a sample with a pulse of electromagnetic radiation, said pulse having a plurality of frequencies in the range from 25 GHz to 100 THz;
 (b) determining a first parameter at least related to the amplitude of the radiation, which is either reflected from and/or transmitted by the sample, in the time domain;
 (c) calculating the value of the first parameter at a first time value relative to the value of the first parameter at a second time value; and
 (d) generating an image of the sample by plotting the value of the first parameter calculated in step (c) for different spatial points over an area of the sample, wherein the time interval between the first and second time values is constant for all points used to generate the image.

28. method of imaging a sample, the method comprising:
 (a) irradiating a sample with a pulse of electromagnetic radiation, said pulse having a plurality of frequencies in the range from 25 GHz to 100 THz;
 (b) determining a first parameter at least related to the amplitude of the radiation, which is either reflected from and/or transmitted by the sample, in the time domain; and
 (c) generating an image of the sample by plotting the value of the first parameter at a first time value, said first time value being determined by:
   (i) selecting n regions of said sample, where n is an integer of at least 2,
   (ii) producing n time domain spectra of a second parameter which is at least related to the amplitude of the radiation reflected from and/or transmitted by the sample, where the nth spectra is obtained by averaging the second parameter across the nth region and plotting this averaged value, as it varies with delay time;
   (iii) determining the first time value by comparing at least two of the n spectra derived in step (ii).

29. A method according to claim 28, wherein step (ii) comprises generating a preliminary image of an area of the sample by plotting a preliminary imaging parameter which is at least related to the amplitude of the radiation reflected from and/or transmitted by the sample; and selecting said n regions from said preliminary image.

30. A method according to claim 29, wherein said n regions are selected such that said n regions being selected such that the level of the preliminary imaging parameter within each region is substantially constant and the level of the preliminary imaging parameter is different between at least two of the said regions.

31. A method according to either of claim 29, wherein the preliminary imaging parameter is the value of the first and/or second parameter at a time which corresponds to a physical feature of the time domain spectra of the first and/or second parameter.

32. A method according to claim 29, where n=3 and the value of the preliminary imaging parameter differs between said three selected regions, the first time value being chosen to coincide with a region where there is a difference between the three spectra.

33. A method according to claim 28, wherein each spectra is normalised to the value of a third parameter at a time value which coincides with a physical feature of the second parameter with respect to time, prior to comparing the spectra.

34. A method according to claim 28, wherein step (iii) comprises performing a mathematical operation to combine at least two of the spectra.

35. A method according to claim 34, wherein the difference between at least two of the spectra is calculated.

36. A method according to claim 34, wherein at least one of the spectra is divided by another one of said n spectra.

37. A method according to claim 28, wherein n=2.

38. A method according to claim 28, wherein the second parameter and the first parameter are the same.

39. An apparatus for imaging a sample, the apparatus comprising:
 a source for irradiating a sample with a pulse of electromagnetic radiation, said pulse having a plurality of frequencies in the range from 25 GHz to 100 Thz;
 detector means for detecting the amplitude of radiation reflected from and/or transmitted by the sample;
 means for determining a first parameter at least related to the amplitude of the radiation in the time domain;
 calculating means configured to calculate the value of the first parameter at a first time value with respect to the value of the first parameter at a second time value, wherein the second time value coincides with a physical feature of the dataset of the first parameter with respect to time, and
 imaging means for generating an image of the sample by plotting the value of the first parameter calculated by the calculating means for different spatial points over an area of the sample.

40. An apparatus according to claim 39, wherein the calculating means is configured to calculate the value of the first parameter for the first time value with respect to the second time value for a plurality of different first time values for each point of the sample used to generate the image.

41. An apparatus according to claim 40, further comprising means to produce a plurality of images for different first time values.

42. An apparatus according to claim 41, wherein the apparatus comprises means to scan through the plurality of images.

43. An apparatus according to claim 39, wherein the first time value is constant for all points used to generate a single image.

44. An apparatus according to claim 43, further comprising means to optimise contrast in the image by selecting the first time value which provides the best contrast.

45. An apparatus according to claim 39, wherein the time interval between the first time value and the second time value is constant for all points used to generate a single image.

46. An apparatus according to claim 45, further comprising means to optimise contrast in an image by selecting the fixed time interval which provides the best contrast.

47. An apparatus for imaging a sample, the apparatus comprising:
 a source for irradiating a sample with a pulse of electromagnetic radiation, said pulse having a plurality of frequencies in the range from 25 GHz to 100 THz;
 detector means for detecting the amplitude of radiation reflected from and/or transmitted by the sample;
 means for determining a first parameter at least related to the amplitude of the radiation in the time domain;

calculating means configured to calculate the value of the first parameter at a first time value with respect to the value of the first parameter at a second time value, and imaging means for generating an image of the sample by plotting the value of the first parameter calculated by the calculating means for different spatial points over an area of the sample, wherein the time interval between the first and second time intervals is constant for all points used to generate the image.

48. An apparatus for imaging a sample, the apparatus comprising:
- (a) means for irradiating a sample with a pulse of electromagnetic radiation, said pulse having a plurality of frequencies in the range from 25 GHz to 100 THz;
- (b) means for determining a first parameter, at least related to the amplitude of the radiation, which is either reflected from and/or transmitted by the sample, in the time domain; and
- (c) means for generating an image of the sample by using the value of the first parameter at a first time value, said apparatus being configured to determine said first time value by:
- (i) selecting n regions of said sample, where n is an integer of at least 2;
- (ii) producing n spectra in the time domain, where the nth spectra is obtained by plotting a second parameter which is at least related to the amplitude of the radiation reflected from and/or transmitted by the sample, averaged across the nth area, against delay time;
- iii) determining the first time value by comparing at least two of the n spectra.

* * * * *